(12) United States Patent
Staebler et al.

(10) Patent No.: US 12,017,389 B2
(45) Date of Patent: Jun. 25, 2024

(54) METHODS FOR MANUFACTURING AND DISTRIBUTING SEMI-RIGID ACOUSTIC COUPLING ARTICLES AND PACKAGING FOR ULTRASOUND IMAGING

(71) Applicant: Decision Sciences Medical Company, LLC, Poway, CA (US)

(72) Inventors: Zachary Staebler, Poway, CA (US); Allan Wegner, Poway, CA (US)

(73) Assignee: DECISION SCIENCES MEDICAL COMPANY, LLC, Poway, CA (US)

( * ) Notice: Subject to any disclaimer, the term of this patent is extended or adjusted under 35 U.S.C. 154(b) by 112 days.

(21) Appl. No.: 17/435,504

(22) PCT Filed: Mar. 6, 2020

(86) PCT No.: PCT/US2020/021456
§ 371 (c)(1),
(2) Date: Sep. 1, 2021

(87) PCT Pub. No.: WO2020/181213
PCT Pub. Date: Sep. 10, 2020

(65) Prior Publication Data
US 2022/0134608 A1    May 5, 2022

Related U.S. Application Data

(60) Provisional application No. 62/814,835, filed on Mar. 6, 2019.

(51) Int. Cl.
*B29C 39/00*    (2006.01)
*B29C 35/08*    (2006.01)
(Continued)

(52) U.S. Cl.
CPC ............ *B29C 39/003* (2013.01); *B29C 35/08* (2013.01); *B29C 39/22* (2013.01); *B29C 39/38* (2013.01);
(Continued)

(58) Field of Classification Search
None
See application file for complete search history.

(56) References Cited

U.S. PATENT DOCUMENTS 4,105,018 A    8/1978    Greenleaf et al.
4,110,755 A    8/1978    Zottl
(Continued)

FOREIGN PATENT DOCUMENTS

CA    2427186 A1    5/2001
CA    2852801 A1    5/2013
(Continued)

OTHER PUBLICATIONS

Laferrère, C. A., F. O. Andersson, and R. Roy. "[25] Syntheses of water-soluble polyacrylamide-containing sialic acid." Methods in Enzymology. Vol. 242. Academic Press, 1994. 271-280. (Year: 1994).*
(Continued)

*Primary Examiner* — Benjamin A Schiffman
(74) *Attorney, Agent, or Firm* — Perkins Coie LLP

(57) ABSTRACT

Disclosed are methods for scalable, cost-effective, and rapid production manufacturing and packaging a semi-rigid acoustic coupling medium that can be used for ultrasound diagnostic and treatment systems and techniques. In some aspects, a method includes forming a staged solution by adding together a stock solution comprising a monomer and a block copolymer in deoxygenated water and a primed solution comprising a covalent crosslinking agent and a catalyst; forming a gel-sol by mixing the staged solution
(Continued)

with a first network activator solution comprising a monomer activator and a second network activator solution comprising a block copolymer activator; dispensing the gel-sol into a mold; and curing the gel-sol in the mold to produce a semi-rigid acoustic coupling material, where the method is carried under an inert atmosphere.

23 Claims, 21 Drawing Sheets

(51) Int. Cl.
| | | |
|---|---|---|
| *B29C 39/22* | (2006.01) | |
| *B29C 39/38* | (2006.01) | |
| *A61B 8/00* | (2006.01) | |
| *B29K 105/00* | (2006.01) | |
| *B29L 31/00* | (2006.01) | |

(52) U.S. Cl.
CPC ..... *A61B 8/4281* (2013.01); *B29K 2105/0002* (2013.01); *B29K 2105/0061* (2013.01); *B29L 2031/752* (2013.01)

(56) References Cited

U.S. PATENT DOCUMENTS

| | | |
|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,039,774 A | 8/1991 | Shikinamie et al. |
| 5,078,149 A * | 1/1992 | Katsumata ........... A61B 8/4281 73/644 |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A | 3/1995 | Orr et al. |
| 5,417,218 A | 5/1995 | Spivey et al. |
| 5,445,144 A | 8/1995 | Wodicka et al. |
| 5,465,722 A | 11/1995 | Fort et al. |
| 5,522,878 A | 6/1996 | Montecalvo |
| 5,533,510 A | 7/1996 | Koch, III et al. |
| 5,608,690 A | 3/1997 | Hossack et al. |
| 5,623,928 A | 4/1997 | Wright et al. |
| 5,753,095 A | 5/1998 | Alpenfels et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A | 3/2000 | Larson |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,107,365 A | 8/2000 | Bertozzi et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 | 11/2003 | Levkovitz et al. |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,207,939 B2 | 4/2007 | Husher |
| 7,226,456 B2 | 6/2007 | O'Neil et al. |
| 7,291,119 B1 | 11/2007 | de Guise et al. |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| RE42,194 E | 3/2011 | Foley et al. |
| 7,905,836 B2 | 3/2011 | Dan |
| 7,917,317 B2 | 3/2011 | McKeon |
| 7,938,777 B2 | 5/2011 | Amiot et al. |
| 7,938,778 B2 | 5/2011 | Sakai |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |
| 8,253,578 B2 | 8/2012 | Watabe et al. |
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |

(56) References Cited

U.S. PATENT DOCUMENTS

| | | | |
|---|---|---|---|
| 8,556,834 B2 | 10/2013 | Gertner | |
| 8,565,860 B2 | 10/2013 | Kimchy et al. | |
| 8,626,267 B2 | 1/2014 | Lavallee | |
| 8,675,939 B2 | 3/2014 | Moctezuma de la Barrera | |
| 8,771,188 B2 | 7/2014 | Schers et al. | |
| 8,774,900 B2 | 7/2014 | Buly et al. | |
| 8,814,810 B2 | 8/2014 | Roche et al. | |
| 8,864,686 B2 | 10/2014 | Roche et al. | |
| 8,880,152 B2 | 11/2014 | Lavallee | |
| 8,909,325 B2 | 12/2014 | Kimchy et al. | |
| 8,939,909 B2 | 1/2015 | Wegner | |
| 8,986,609 B2 * | 3/2015 | Rau | A61L 2/10 564/153 |
| 9,060,794 B2 | 6/2015 | Kang et al. | |
| 9,101,394 B2 | 8/2015 | Arata et al. | |
| 9,174,065 B2 | 11/2015 | Gertner | |
| 9,196,046 B2 | 11/2015 | Meyer | |
| 9,220,571 B2 | 12/2015 | Lavallee | |
| 9,244,169 B2 | 1/2016 | Fan et al. | |
| 9,248,001 B2 | 2/2016 | Colombet et al. | |
| 9,352,171 B2 | 5/2016 | Gertner | |
| 9,387,276 B2 | 7/2016 | Sun et al. | |
| 9,420,999 B2 | 8/2016 | Wegner | |
| 9,572,548 B2 | 2/2017 | Moctezuma de la Barrera | |
| 9,597,058 B2 | 3/2017 | Kanayama et al. | |
| 9,844,359 B2 | 12/2017 | Gerbaulet et al. | |
| 9,872,667 B2 | 1/2018 | Wegner | |
| 10,085,722 B2 | 10/2018 | Wegner | |
| 10,321,889 B2 | 6/2019 | Wegner | |
| 10,336,896 B2 * | 7/2019 | Zheng | C08B 37/0039 |
| 10,426,429 B2 | 10/2019 | Kruse et al. | |
| 10,743,838 B2 * | 8/2020 | Freiburg | A61B 8/44 |
| 10,975,205 B2 * | 4/2021 | Illeperuma | G01L 1/142 |
| 11,154,274 B2 * | 10/2021 | Wegner | A61K 49/226 |
| 2002/0068871 A1 | 6/2002 | Mendlein et al. | |
| 2002/0099290 A1 | 7/2002 | Haddad | |
| 2002/0122536 A1 | 9/2002 | Kerrien et al. | |
| 2002/0188229 A1 | 12/2002 | Ryaby et al. | |
| 2003/0036702 A1 | 2/2003 | Davidsen | |
| 2003/0125628 A1 | 7/2003 | Song et al. | |
| 2003/0233045 A1 | 12/2003 | Vaezy | |
| 2004/0066708 A1 | 4/2004 | Ogawa | |
| 2004/0236223 A1 | 11/2004 | Barnes et al. | |
| 2005/0101861 A1 | 5/2005 | Satoh | |
| 2005/0101867 A1 | 5/2005 | Johnson et al. | |
| 2005/0113698 A1 | 5/2005 | Kristoffersen | |
| 2005/0203399 A1 | 9/2005 | Vaezy | |
| 2005/0215893 A1 | 9/2005 | Barnes et al. | |
| 2006/0004290 A1 | 1/2006 | Smith et al. | |
| 2006/0119223 A1 | 6/2006 | Ossman | |
| 2006/0173305 A1 | 8/2006 | Asafusa et al. | |
| 2007/0066897 A1 | 3/2007 | Sekins et al. | |
| 2007/0156050 A1 | 7/2007 | Barnes et al. | |
| 2007/0226976 A1 | 10/2007 | Zipparo et al. | |
| 2007/0239001 A1 | 10/2007 | Mehi et al. | |
| 2007/0239002 A1 | 10/2007 | Alam | |
| 2007/0265690 A1 | 11/2007 | Lichtenstein et al. | |
| 2007/0276238 A1 | 11/2007 | Sudol | |
| 2008/0051655 A1 * | 2/2008 | Sato | A61B 8/12 600/439 |
| 2008/0110263 A1 | 5/2008 | Klessel et al. | |
| 2008/0119737 A1 | 5/2008 | Urbano et al. | |
| 2008/0200810 A1 | 8/2008 | Buchalter | |
| 2008/0208055 A1 | 8/2008 | Bertram et al. | |
| 2008/0281202 A1 | 11/2008 | Fraser et al. | |
| 2008/0281237 A1 | 11/2008 | Slayton et al. | |
| 2009/0043206 A1 | 2/2009 | Towfiq et al. | |
| 2009/0093737 A1 | 4/2009 | Gerbaulet et al. | |
| 2009/0124871 A1 | 5/2009 | Arshak et al. | |
| 2009/0306497 A1 | 12/2009 | Manzke et al. | |
| 2010/0029789 A1 | 2/2010 | Chen | |
| 2010/0179425 A1 | 7/2010 | Zadicario | |
| 2010/0204577 A1 | 8/2010 | Sekins et al. | |
| 2010/0268072 A1 | 10/2010 | Hall et al. | |
| 2010/0274139 A1 | 10/2010 | Fukukita et al. | |
| 2010/0280379 A1 | 11/2010 | Satoh | |
| 2010/0286518 A1 | 11/2010 | Lee et al. | |
| 2010/0286527 A1 | 11/2010 | Cannon | |
| 2011/0092862 A1 | 4/2011 | Chivers | |
| 2011/0264012 A1 | 10/2011 | Lautzenhiser et al. | |
| 2012/0029345 A1 | 2/2012 | Mahfouz et al. | |
| 2012/0238875 A1 | 9/2012 | Savitsky et al. | |
| 2012/0253071 A1 | 10/2012 | Rau et al. | |
| 2012/0281507 A1 | 11/2012 | Rikoski | |
| 2013/0060121 A1 | 3/2013 | Patwardhan et al. | |
| 2013/0102875 A1 | 4/2013 | Dogra et al. | |
| 2013/0123635 A1 | 5/2013 | Wegner | |
| 2013/0144135 A1 | 6/2013 | Mahfouz et al. | |
| 2013/0144166 A1 | 6/2013 | Specht et al. | |
| 2013/0150863 A1 | 6/2013 | Baumgartner | |
| 2013/0165005 A1 | 6/2013 | Berard-Anderson et al. | |
| 2013/0218013 A1 | 8/2013 | Barthe et al. | |
| 2014/0163377 A1 | 6/2014 | Kang et al. | |
| 2014/0180116 A1 | 6/2014 | Lindekugel et al. | |
| 2014/0353248 A1 | 12/2014 | Kuraray | |
| 2015/0018682 A1 | 1/2015 | Schers et al. | |
| 2015/0038613 A1 | 2/2015 | Sun et al. | |
| 2015/0080725 A1 | 3/2015 | Wegner | |
| 2015/0088040 A1 | 3/2015 | Barthe et al. | |
| 2015/0133788 A1 | 5/2015 | Mauldin, Jr. et al. | |
| 2015/0164467 A1 | 6/2015 | Suetoshi et al. | |
| 2015/0182191 A1 | 7/2015 | Caluser et al. | |
| 2015/0274805 A1 | 10/2015 | Annabi et al. | |
| 2015/0313572 A1 | 11/2015 | Gerbaulet et al. | |
| 2016/0000409 A1 | 1/2016 | Bruder et al. | |
| 2016/0083574 A1 | 3/2016 | Zheng et al. | |
| 2016/0100821 A1 | 4/2016 | Eggers et al. | |
| 2016/0176128 A1 | 6/2016 | Zhao et al. | |
| 2016/0242736 A1 | 8/2016 | Freiburg | |
| 2016/0270763 A1 | 9/2016 | Hayes et al. | |
| 2016/0354520 A1 | 12/2016 | Sun et al. | |
| 2017/0100092 A1 | 4/2017 | Kruse et al. | |
| 2017/0368333 A1 | 12/2017 | Loudin et al. | |
| 2018/0126677 A1 | 5/2018 | Zhao et al. | |
| 2018/0240366 A1 | 8/2018 | Felsinger et al. | |
| 2018/0244858 A1 | 8/2018 | Illeperuma et al. | |
| 2019/0070826 A1 * | 3/2019 | Zhao | B32B 27/08 |
| 2019/0167234 A1 | 6/2019 | Wegner | |
| 2019/0200957 A1 | 7/2019 | Freiburg et al. | |
| 2020/0138409 A1 | 5/2020 | Lindekugel et al. | |
| 2020/0337674 A1 | 10/2020 | Wegner | |
| 2021/0361259 A1 | 11/2021 | Wegner | |
| 2022/0106424 A1 * | 4/2022 | Staebler | C08B 37/0084 |
| 2022/0192634 A1 | 6/2022 | Freiburg | |

FOREIGN PATENT DOCUMENTS

| | | |
|---|---|---|
| CN | 100354651 C | 12/2007 |
| CN | 101325913 A | 12/2008 |
| CN | 102258399 B | 11/2012 |
| CN | 104169739 A | 11/2014 |
| CN | 104311841 A | 1/2015 |
| CN | 105778125 A | 7/2016 |
| EP | 952461 A2 | 10/1999 |
| EP | 1707124 A2 | 4/2006 |
| EP | 1795917 A2 | 6/2007 |
| EP | 1854406 A1 | 11/2007 |
| EP | 1955668 A1 | 8/2008 |
| EP | 2033579 A1 | 3/2009 |
| GB | 2379392 B | 3/2003 |
| GB | 2472066 A | 1/2011 |
| IL | 232148 A | 7/2019 |
| JP | 55051351 A | 4/1980 |
| JP | 58195550 A | 11/1983 |
| JP | 60048736 A | 3/1985 |
| JP | 62117535 A | 5/1987 |
| JP | H03114453 | 5/1991 |
| JP | 8038473 A | 2/1996 |
| JP | 2000041980 A | 2/2000 |
| JP | 2000166922 | 6/2000 |
| JP | 2000287988 | 10/2000 |
| JP | 2001515924 | 9/2001 |
| JP | 2003190157 A | 7/2003 |
| JP | 2004147852 A | 5/2004 |

(56) References Cited

FOREIGN PATENT DOCUMENTS

| | | | |
|---|---|---|---|
| JP | 2005152608 A | 6/2005 | |
| JP | 2005527336 A | 9/2005 | |
| JP | 2010082425 A | 4/2010 | |
| JP | 2011062531 | 3/2011 | |
| JP | 2011177461 A | 9/2011 | |
| JP | 2012002586 A | 1/2012 | |
| JP | 2013056156 A | 3/2013 | |
| JP | 2018506416 A | 3/2018 | |
| WO | 2002024094 A2 | 3/2002 | |
| WO | 2007023477 A2 | 3/2007 | |
| WO | 2007069156 A1 | 6/2007 | |
| WO | 2009009064 A1 | 1/2009 | |
| WO | 2009020617 A1 | 2/2009 | |
| WO | 2009063421 A1 | 5/2009 | |
| WO | 2013066821 A2 | 5/2013 | |
| WO | 2013103956 A1 | 7/2013 | |
| WO | 2014128593 A1 | 8/2014 | |
| WO | 2014150780 A2 | 9/2014 | |
| WO | 2014150961 A1 | 9/2014 | |
| WO | 2014186904 A1 | 11/2014 | |
| WO | 2015038554 A2 | 3/2015 | |
| WO | 2016044830 A1 | 3/2016 | |
| WO | 2016138257 A1 | 9/2016 | |
| WO | 2016149427 A1 | 9/2016 | |
| WO | 2017164902 A1 | 9/2017 | |

OTHER PUBLICATIONS

Office Action mailed Jul. 12, 2022 in Chinese Patent Application No. 202080021490.7, with English translation, 18 pages.

Office Action mailed Jul. 28, 2022 in Korean Patent Application No. 2017-7027091, machine translation obtained from USPTO Global Dossier at <https://globaldossier.uspto.gov/#/>, 28 pages.

Sun, J.Y. et al., "Highly stretchable and tough hydrogels," Nature, vol. 489, Sep. 6, 2012, 21 pages.

Australian Exam Report mailed Nov. 1, 2019 for Australian Application No. 2016233279, filed on Mar. 16, 2016 (3 pages).

Australian Exam Report mailed Oct. 18, 2019 for Australian Application No. 2016222637, filed on Feb. 25, 2016 (3 pages).

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

Cao, Z. et al., "Fabrication and properties of thermosensitive organic/inorganic hybrid hydrogel thin films," Langmuir, American Chemical Society, vol. 24, No. 10, May 20, 2008, pp. 5543-5551.

Chiao, R., "Coded Excitation for Diagnostic Ultrasound: A System Developer's Perspective," *IEEE Transactions on Ultrasonics, Ferroelectrics, and Frequency Control*, 52(2):160-170, Feb. 2005.

Choe, J.W., et al., "Volumetric real-time imaging using a CMUT ring array," IEEE Transactions on Ultrasonics, Ferroelectrics, and Frequency Control, 59(6):1201-1211, Jun. 2012.

Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.

European Search Report mailed on Apr. 19, 2017 for European Application No. 14844538.0, filed on Sep. 9, 2014 (10 pages).

European Search Report mailed on Feb. 1, 2019 for European Application No. 16756353.5, filed on Feb. 25, 2016 (14 pages).

European Search Report mailed on Jun. 29, 2015 for European Application No. 12845256.2, filed on Oct. 29, 2012 (8 pages).

European Search Report mailed on Nov. 9, 2018 for European Application No. 16765701.4, filed on Mar. 16, 2016 (6 pages).

Exam Report mailed Oct. 18, 2019 for Australian Application No. 2016222637, filed on Feb. 25, 2016 (3 pages).

Exam Report mailed on Feb. 26, 2019 for Singapore Application No. 11201706953Y, filed on Feb. 25, 2016 (6 pages).

Extended European Search Report mailed on Feb. 15, 2019 for European Application No. 16765701.4, filed on Mar. 16, 2016 (14 pages).

Extended European Search Report mailed on Jul. 2, 2019 for European Application No. 16756353.5, filed on Feb. 25, 2016 (14 pages).

Extended Search Report mailed on Jun. 18, 2019 for European Application No. 16854507.7, filed on Oct. 7, 2016 (11 pages).

Hunter, A.J., et al., "A Comparison of Fast Factorised Back-Projection and Wavenumber Algorithms for SAS Image Reconstruction," Proceedings of the World Congress on Ultrasonics, 4 pages, (2003).

International Search Report and Written Opinion mailed Jul. 16, 2020 for International App. PCT/US20/29564 filed Apr. 23, 2020, 11 pages.

International Search Report and Written Opinion mailed on Dec. 29, 2016 for International Application No. PCT/US2016/056159, filed on Oct. 7, 2016 (7 pages).

International Search Report and Written Opinion mailed on Jul. 2, 2020 for International Application No. PCT/US2020/021456, filed on Mar. 6, 2020, 16 pages.

International Search Report and Written Opinion mailed on Jul. 6, 2016 for International Application No. PCT/US2016/019554, filed on Feb. 25, 2016 (12 pages).

International Search Report and Written Opinion mailed on Mar. 3, 2015 for International Application No. PCT/US2014/054855, filed on Sep. 9, 2014 (11 pages).

International Search Report and Written Opinion mailed on May 15, 2013 for International Application No. PCT/US2012/062435, filed on Oct. 29, 2012 (9 pages).

International Search Report and Written Opinion mailed on May 18, 2020 for International Application No. PCT/US20/18123, filed on Feb. 13, 2020 (11 pages).

Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.

Jensen, J.A., et al., "Synthetic Aperture Ultrasound Imaging," Ultrasonics, 44(Suppl 1):e5-e15, Dec. 2006.

Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.

Kundur, D., et al., "A Novel Blind Deconvolution Scheme for Image Restoration Using Recursive Filtering," IEEE Transactions on Signal Processing, 46(2):375-390, Feb. 1998.

Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.

Misaridis, T., "Use of Modulated Excitation Signals in Medical Ultrasound. Part II: Design and Performance for Medical Imaging Applications," *IEEE Transactions on Ultrasonics, Ferroelectrics, and Frequency Control*, 52(2):192-207, Feb. 2005.

Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.

O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.

Office Action mailed Jun. 4, 2019 for Japanese Application No. 2017-187288, filed on Oct. 29, 2012 (3 pages).

Office Action mailed Oct. 29, 2019 for Japanese Application No. 2018-145683, filed on Sep. 9, 2014 (3 pages).

Office Action mailed on Dec. 4, 2019 for Chinese Application No. 201680023999.9, filed on Feb. 25, 2016 (23 pages).

Office Action mailed on Jul. 3, 2018 for Japanese Application No. 2017-187288, filed on Oct. 29, 2012 (6 pages).

Office Action mailed on Sep. 13, 2016 for Japanese Application No. 2014-539114, filed on Oct. 29, 2012 (4 pages).

(56) References Cited

OTHER PUBLICATIONS

Office Action mailed on Sep. 19, 2017 for Japanese Application No. 2016-542050, filed on Sep. 9, 2014 (15 pages).
Office Action mailed on Sep. 2, 2015 for Chinese Application No. 201280065031.4, filed on Oct. 29, 2012 (26 pages).
Office Action mailed Sep. 23, 2020 in Israel Patent Application No. 254158, 3 pages.
Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.
Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.
Second Office Action issued Jul. 14, 2020 for Chinese Patent Application No. 201680023999.9 (41 pages).
Singapore Exam Report mailed on Feb. 26, 2019 for Singapore Application No. 11201706953Y, filed on Feb. 25, 2016 (6 pages).
Singapore Search Report mailed on Sep. 24, 2018 for Singapore Application No. 11201706953Y, filed on Feb. 25, 2016 (13 pages).
Singapore Written Opinion mailed on Jul. 10, 2017 for Singapore Application No. 11201601906P, filed on Sep. 9, 2014 (8 pages).
Singapore Written Opinion mailed on Jun. 21, 2018 for Singapore Application No. 11201707641P, filed on Mar. 16, 2016 (8 pages).
Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.
European Search Report mailed Oct. 26, 2022 in European Patent Application No. 20767211.4, 13 pages.
European Search Report mailed on Oct. 17, 2022 in European Patent Application No. 20756147.3, 6 pages.
Extended European Search Report mailed Jan. 26, 2023 for European Patent Application No. 20767211.4, 11 pages.
Low, Z.W. et al., "The role of hydrogen bonding in alginate/poly(acrylamide-co-dimethylacrylamide) and alginate/poly(ethylene glycol) methyl ether methacrylate-based tough hybrid hydrogels." Royal Society of Chemistry, 2015, 5, 8 pages.
Low, Z.W. et al., Supporting Information. "The role of hydrogen bonding in alginate/poly(acrylamide-co-dimethylacrylamide) and alginate/poly(ethylene glycol) methyl ether methacrylate-based tough hybrid hydrogels." Royal Society of Chemistry, 2015, 5, 5 pages.
Office Action mailed Jan. 14, 2020 for Japanese Application No. 2017-563504, filed on Feb. 25, 2016 (14 pages).
Second Office Action mailed Jan. 3, 2023 in Chinese Patent Application No. 202080021490.7, English translation, 16 pages.
Office Action mailed Feb. 23, 2023 in Korean Patent Application No. 2017-7027091, 11 pages, with English Translation.
Examination Report mailed Mar. 10, 2023 in Canadian Patent Application No. 2,977,975, 4 pages.
Notice of Reasons for Rejection mailed Sep. 26, 2023 in Japanese Patent Application No. 2021-552570, English Translation, 4 pages.
Notice of Requisition mailed Mar. 10, 2023 in Canadian Patent Application No. 2,977,975, 4 pages.
Third Office Action mailed Jul. 10, 2023 in Chinese Patent Application No. 202080021490.7, English translation, 14 pages.

\* cited by examiner

METHODS FOR MANUFACTURING AND DISTRIBUTING SEMI-RIGID ACOUSTIC COUPLING ARTICLES AND PACKAGING FOR ULTRASOUND IMAGING

CROSS-REFERENCE TO RELATED APPLICATIONS

This patent document is a National Phase Application of International Patent Application No. PCT/US20/21456 titled "METHODS FOR MANUFACTURING AND DISTRIBUTING SEMI-RIGID ACOUSTIC COUPLING ARTICLES AND PACKAGING FOR ULTRASOUND IMAGING" filed on Mar. 6, 2020, which claims priorities to and benefits of U.S. Provisional Patent Application No. 62/814,835 titled "METHODS FOR MANUFACTURING AND DISTRIBUTING SEMI-RIGID ACOUSTIC COUPLING ARTICLES AND PACKAGING FOR ULTRASOUND IMAGING" filed on Mar. 6, 2019. The entire content of the aforementioned patent applications are incorporated by reference as part of the disclosure of this patent document.

TECHNICAL FIELD

This patent document relates to methods, devices and articles for an acoustic coupling medium useful for ultrasound imaging.

BACKGROUND

Acoustic imaging is an imaging modality that employs the properties of sound waves traveling through a medium to render a visual image. High frequency acoustic imaging has been used as an imaging modality for decades in a variety of biomedical fields to view internal structures and functions of animals and humans. High frequency acoustic waves used in biomedical imaging may operate in different frequencies, e.g., between 1 and 20 MHz, or even higher frequencies, and are often termed ultrasound waves. Some factors, including inadequate spatial resolution and tissue differentiation, can lead to less than desirable image quality using conventional techniques of ultrasound imaging, which can limit its use for many clinical indications or applications.

SUMMARY

Disclosed are methods for manufacturing and packaging a semi-rigid acoustic coupling medium (SACM), which can be embodied as a semi-rigid hydrogel interface pad, that provides an acoustic coupling medium for ultrasound diagnostic and treatment techniques.

In some aspects, a method of manufacturing an acoustic coupling material includes (a) forming a staged solution by adding together a stock solution comprising a monomer and a polymer in deoxygenated water and a primed solution comprising a covalent crosslinking agent and a catalyst; (b) forming a gel-sol by mixing the staged solution with a first network activator solution comprising a monomer activator and a second network activator solution comprising a polymer activator; (c) dispensing the gel-sol into a mold; and (d) curing the gel-sol in the mold to produce a semi-rigid acoustic couplant, wherein the method is carried under an inert atmosphere.

In some aspects, a method of manufacturing a hydrogel includes (a) heating a first solution comprising a 1° network component and a 2° network component in deoxygenated water to lower a viscosity of the solution; (b) cooling the first solution to about 23° C. and adding a second solution comprising 1° network crosslinker and a catalyst to form a third solution; (c) optionally, adding a photoinitiator to the second solution prior to adding the second solution to the first solution; and (d) cooling the third solution to about 15° C. and adding a chilled 1° network activator solution and a chilled 2° network activator solution to the third solution simultaneously, wherein upon adding the chilled 1° network activator solution and a chilled 2° network activator solution, the 1° network component and the 2° network component polymerize to form a gel-sol; and (e) dispensing the gel-sol into a mold to form the hydrogel, wherein each of steps (a)-(e) are carried out under and inert atmosphere.

In some aspects, a method of manufacturing a hydrogel comprising sodium alginate block copolymer (P(SA)) and dimethylacrylamide monomer (DMAm) includes (a) preparing a solution comprising sodium alginate (SA) in deoxygenated water and preparing a solution comprising dimethylacrylamide (DMA) in deoxygenated water; (b) filtering the solution comprising the SA to remove aggregated SA and collecting a filtrate of the solution comprising SA; (c) adding the solution comprising DMA to the filtrate of the solution comprising SA to form a stock solution; (d) mixing the stock solution with a solution comprising N',N',N,N-tetramethylethylenediamine (TMED) and N,N'-methylene bisacrylamide (MBA) to form a staged solution; (e) adding to the staged solution a solution comprising a calcium sulfate (CA) and a solution comprising ammonium persulfate (APS) simultaneously, wherein the DMA and SA polymerize to form a gel-sol; (f) dispensing the gel-sol of the polymerized DMA and SA into a mold; (g) placing the mold into oven to cure the gel-sol and optionally, irradiating the gel-solution with light to accelerate curing to form the hydrogel; (h) sealing the hydrogel under an inert atmosphere; and (g) packing the hydrogel into a vehicle for shipment.

In some aspects, an acoustic coupling article includes a semi-rigid acoustic coupling medium (SACM) operable to conform to a receiving body to propagate an acoustic signal within the SACM to and from the receiving body; and a packaging container coupled to the external layer of the SACM, the packing container including a mold casing in which the SACM is produced therein to have at least a portion of its shape defined by the mold casing.

The subject matter described in this patent document can be implemented in specific ways that provide one or more of the following features.

DETAILED DESCRIPTION

Figure 1A:
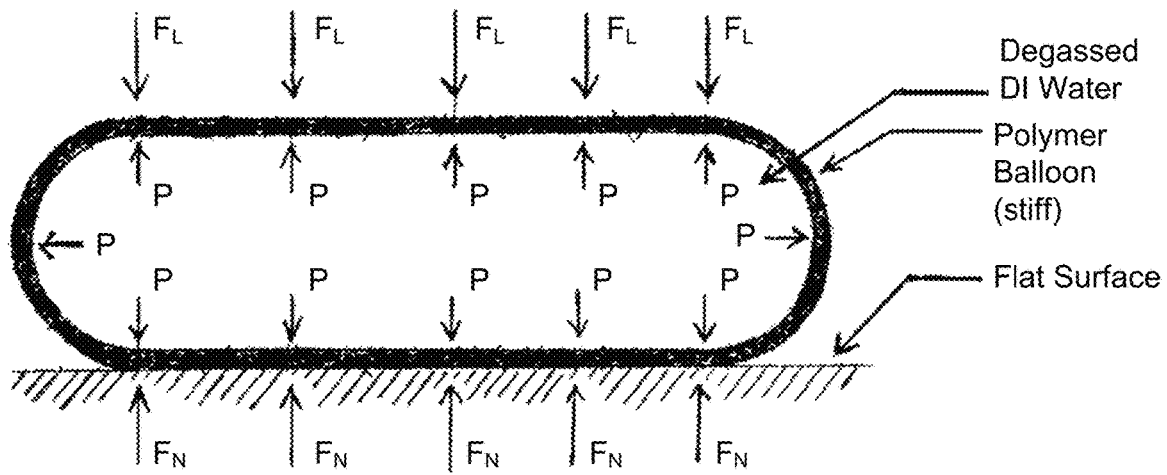
FIGS. 1A and 1B show diagrams illustrating an acoustic couplant which exhibits a lack of conformability to a patient's skin.

Acoustic imaging can be performed by emitting an acoustic waveform (e.g., pulse) within a physical elastic medium, such as a biological medium, including tissue. The acoustic waveform is transmitted from a transducer element (e.g., of an array of transducer elements) toward a target volume of interest (VOI). Propagation of the acoustic waveform in the medium toward the target volume can encounter structures that cause the acoustic waveform to become partly reflected from a boundary between two mediums (e.g., differing biological tissue structures) and partially transmitted. The reflection of the transmitted acoustic waveform can depend on the acoustic impedance difference between the two mediums (e.g., at the interface between two different biological tissue types). For example, some of the acoustic energy of the transmitted acoustic waveform can be scattered back to the transducer at the interface to be received, and processed to extract information, while the remainder may travel on and to the next medium. In some instances, scattering of the reflection may occur as the result of two or more impedances contained in the reflective medium acting as a scattering center. Additionally, for example, the acoustic energy can be refracted, diffracted, delayed, and/or attenuated based on the properties of the medium and/or the nature of the acoustic wave.

Acoustic wave speed and acoustic impedance differences can exist at the interface between the transducer and the medium to receive the acoustic waveform, e.g., referred to as the receiving medium, for propagation of the acoustic waveform toward the target volume, which can disrupt the transmission of the acoustic signal for imaging, range-Doppler measurement, tissue characterization (e.g., Acoustic Radiation Force Impulse—ARFI), or therapeutic applications. Acoustic impedance differences caused due to differing material properties (e.g., material density) of the two mediums and the acoustic wave velocity, such that a substantial amount of the emitted acoustic energy will be reflected at the interface rather than transferred in full across the interface. In typical acoustic (e.g., ultrasound) imaging or therapy applications, for example, a transmission gel is applied to the receiving medium (i.e., the skin of a subject) at the interface where the transducers will make contact to improve the transfer of the acoustic waveform(s) from the transducer to the body and the reception of the returned acoustic waveform(s) from the body back to the transducer. In such applications without the ultrasound gel, the interface may include air as a component of the medium between the receiving medium (e.g., living skin tissue) and the transducer, and an acoustic impedance mismatch in the transducer-to-air and the air-to-body discontinuity causes the scattering (e.g., reflection) of the emitted acoustic energy.

Despite relatively good success in reducing acoustic impedance difference at the interface, when dispensed on the VOI, acoustic transmission gels may contain tiny packets of air that can disrupt the transmission of acoustic signals. Additionally, many patients complain of discomforts with the use of gels dispensed on their skin, e.g., such as temperature, stickiness, or other. More concerning, however, acoustic transmission gels can become contaminated during production or storage, which has led to infections within some patients. For subjects with hair on their skin at the location where the transducer is to be placed, these subjects typically must shave or otherwise remove the external hair which exasperates the trapping of air between the skin and gel.

For non-normal angles of incidence of the acoustic wave relative to the interface, the differences in the acoustic wave speed can result in refraction of the acoustic sound wave. Acoustic wave speed differences at the interface cause the propagation path of longitudinal acoustic waves to refract or change direction according to Snell's Law as a function of the angle of incidence and the acoustic wave speeds either side of the interface. Accumulations of infinitesimal amounts of refraction as the wave propagates in a heterogeneous material results in bending or curvature in the path of the acoustic wave.

As conventional ultrasound (US) imaging assumes that acoustic waves travel in straight lines, refraction along the acoustic path causes degradation and distortion in the resulting image due the ambiguity it creates for the arrival time and location of an acoustic waveform in space for both transmission and reception. A material that matches the acoustic wave speed at the interface significantly reduces the effects of refraction, resulting in a clearer and less ambiguous image. Additionally, a semi-rigid material that has a homogeneous acoustic wave speed throughout will minimize the potential for curvature of acoustic wave paths inside the material.

Ultrasound imaging gained interest in the medical imaging community for portability, multiple anatomic target modalities, safety, and relatively low cost when compared to X-ray, computerized tomography (CT), and magnetic resonance imaging (MRI) techniques. Some modalities focus entirely on cardiology and can create 4-D images of beating ventricles. Other modalities are dedicated calculators that compute fluid flow through tiny corpuscular capillaries in the liver and spleen whereas other modalities simply use the US as a general-purpose machine. Regardless how narrow or broad the application, all US machines suffer from the same limitations engendered from traditional ultrasound design, i.e., loss of image quality at depth and low near field resolution. While the image depth depends mostly on array design and transducer frequency, the obfuscated near field is the result of large impedance mismatch differences between the transducer interface and patient interface and the focal point of the transducer.

Near field convolution is an annoyance encountered in many US diagnostic techniques, especially for synovial joints which are bundles of tendon, fluid, bone, and muscle tightly bound together under a thin, sinewy veil of skin and tissue. This is a ubiquitous problem, and many clinicians have resorted to filling a nitrile rubber glove with tap water to act as a portable, quasi water bath that doubled as a standoff, e.g., any acoustic coupling material providing distance between the transducer interface and patient interface. Simple, cost effective, and fast to implement, this artifice was good enough solution for generating quick non-visceral US images with linear arrays.

Figure 1B:
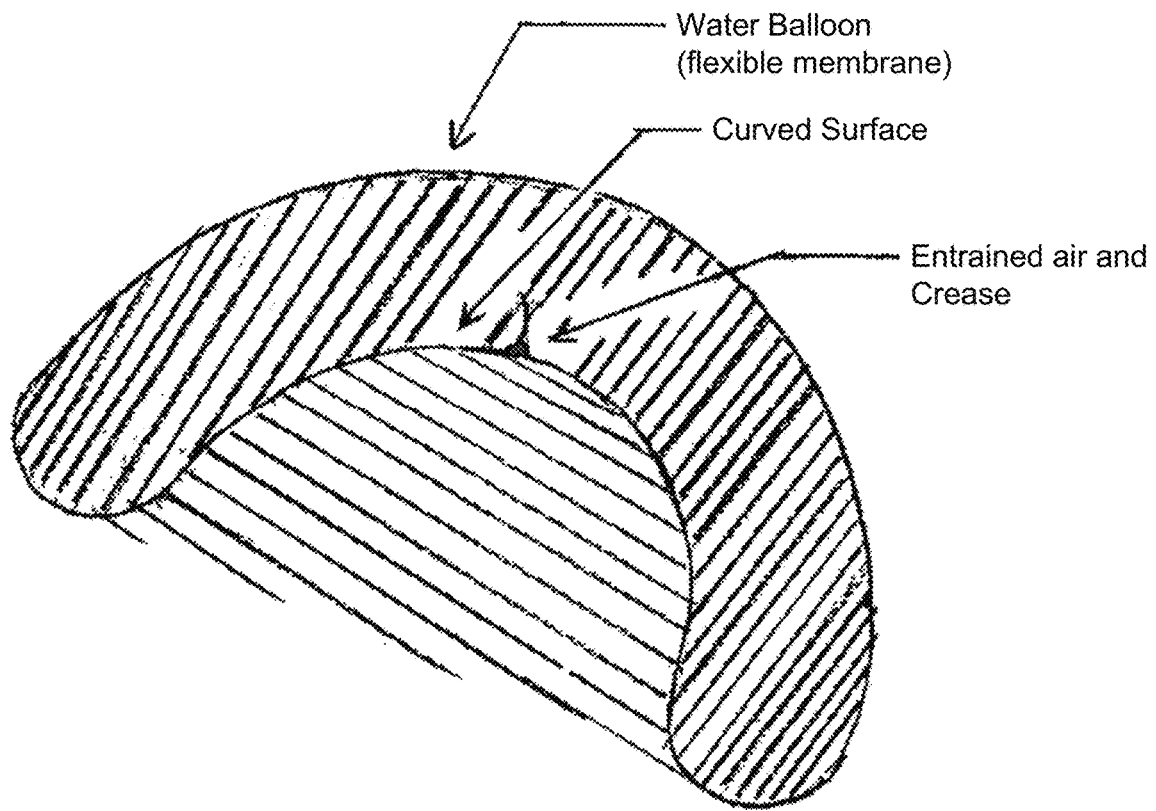

FIGS. 1A and 1B show diagrams illustrating an acoustic couplant which exhibits a lack of conformability to a patient's skin, such as a conventional water balloon couplant. As shown FIG. 1A, the water balloon couplant, in this example, includes a polymer balloon outer membrane that encompasses degassed water (e.g., degassed deionized (DI) water) within the polymer outer membrane. The degassed water entrapped within the outer membrane provides a pressure on the inner surface of the outer membrane, such that the shape of the water balloon couplant is defined by the external forces exerted upon the water balloon—in this example, the external forces include a normal force ($F_N$) exerted by a flat surface in contact with the water balloon couplant and outer force ($F_L$) from the outer environment. The outer membrane of the water balloon couplant is typically flexible, and can be bent to attempt to fit around curved surfaces, as shown by the diagram in FIG. 1B. However, such bending typically creates entrained air and creases at inflexion points along the outer membrane and within the fluidic interior of the water balloon couplant.

Furthermore, for non-linear arrays and non-planar surfaces, technical issues become too challenging for simple water balloons to surmount. Take for an instance a semicircular array for Acoustic Coherent Tomography (ACT) which has several array elements that need to couple to a swath of variegated patient interface geometries during a multi-anatomic target examination. The first challenge with water balloons is contorting the tubular geometry to couple to the transducer interface without creasing on the patient interface, as shown in FIG. 1. Creases will trap air which look like comets in US images with bright spots that shadow out anatomic features and generate artifacts. Even if a few mil-thick (e.g., 0.001 inch-thick) polymer membrane was designed to fit in the array without creasing, the water balloon still lacks conformability needed to scan multiple anatomic targets in a single examination since water is a semi-incompressible fluid ($k=46.4\times10^{-6}$ atm$^{-1}$) and conservation of volume principles apply.

For polymers with thick walls, high young modulus, and low strain before failure the load on the transducer side of the water balloon is directly transmitted to the patient interface without dispersing the load over a larger surface area and without conforming to the non-symmetric patient geometry. Low elastic modulus, high strain before failure, and thin walled polymers might deform more, but are not conformable enough to bridge large gaps between the rigid, symmetrical transducer interface and the asymmetric, deformable patient interface, and are more prone to bursting and rolling during examinations, as illustrated in FIG. 2.

Figure 2:
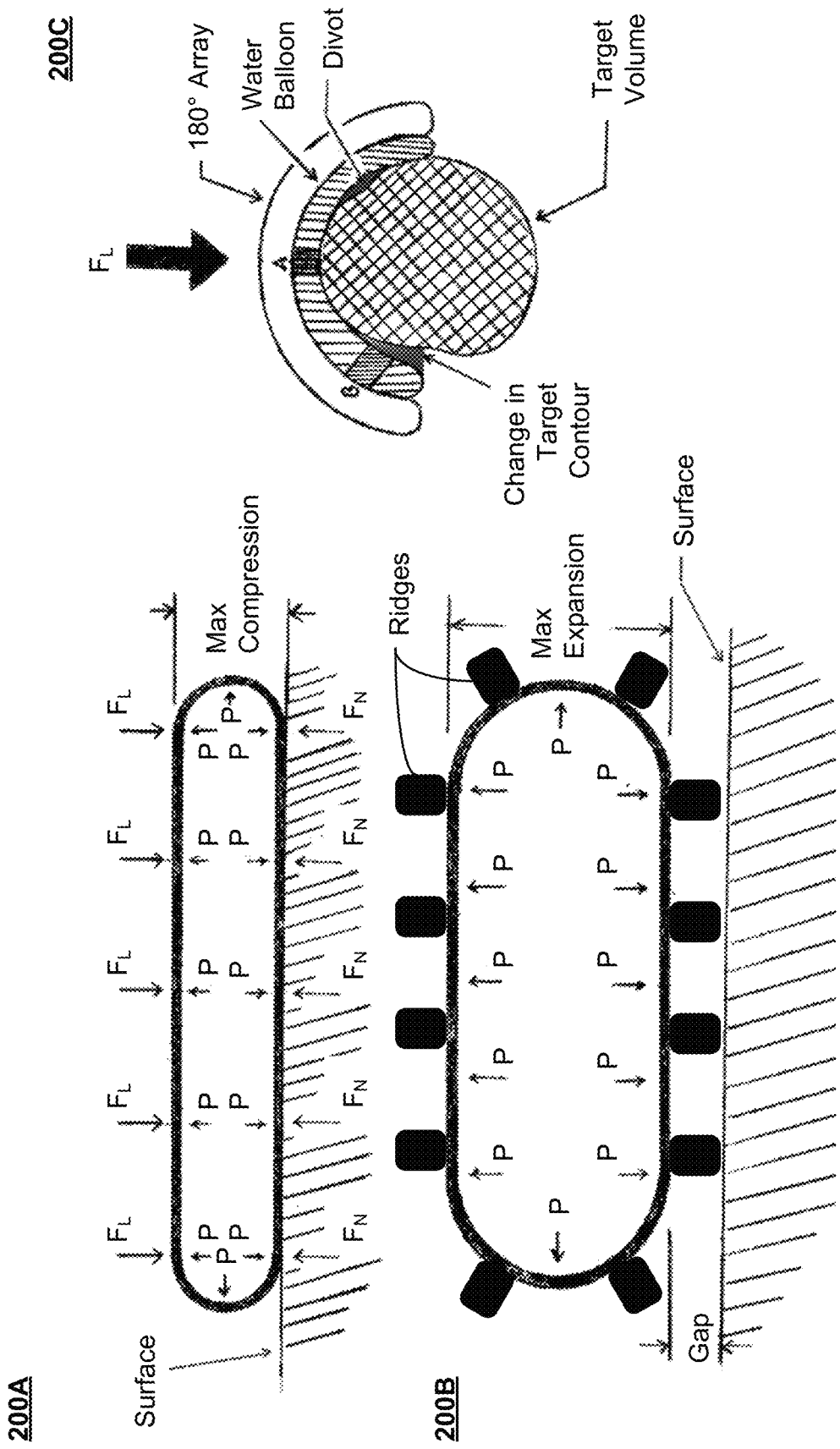
FIG. 2 shows diagrams illustrating conventional acoustic couplants, which can be comprised of polymers that create rigid gaps between the interface of the coupling medium and the patient's skin.

FIG. 2 shows diagrams illustrating a conventional acoustic couplant, such as a water balloon couplant, that is comprised of polymers that create rigid gaps between the interface of the coupling medium and the patient's skin. Diagram 200A shows the example water balloon acoustic couplant in contact with a surface, illustrating maximum compression on the water balloon couplant between applied external forces from a surface in contact with the couplant (normal force $F_N$) and forces ($F_L$) from the surrounding environment. Diagram 200B shows the example water balloon acoustic couplant with folds/creases/ridges formed by the outer polymer membrane of the water balloon slacking when water balloon is bent to conform to the array, trapping air that acts as a strong acoustic reflector. Diagram 200B also shows an example of the water balloon acoustic couplant unable to uniformly couple to the target volume because the water balloon is unable to conform to the contour of the target to fill in the divot and escarpment. Diagram 200C shows an example water balloon couplant in contact with a target volume (e.g., patient's skin of a body part), illustrating how the water balloon couplant may have gaps between the couplant and target volume due to divots and/or changes in the contour of the target.

A more conformable and durable standoff was needed, so thin, semisolid, hydrogel pucks or sheets (e.g., ~1.0-1.5 cm) have been developed to accommodate traditional US imaging in the near field. These hydrogel puck or sheet standoffs aim at minimizing the impedance mismatch between the rigid, symmetrical transducer interface and the asymmetrical, conformable patient interface for linear arrays. More conformable than water balloons, thin hydrogel sheets can fill in divots and escarpments along planar surfaces and form to eclectic curved topography. Additionally, depending on the hydrogel chemistry and morphology, hydrogels can either be sticky for long, static US diagnostic scans or generate a lubricating layer via syneresis when conducting short, dynamic scans under pressure.

Yet, despite greater conformability than water balloons, hydrogels on the current market have a large bulk modulus which increases hydrogel rigidity as the thickness increases. Coupled with low fracture toughness and paraben preservatives, the stiffness and brittleness, the ease of crack propagation, and the ambiguity of health safety render hydrogel standoffs useless in applications where a thick (e.g., >2 cm), tough, and conformable semi-rigid standoff is needed for non-linear arrays like the aforementioned ACT semicircular array.

Disclosed are methods for manufacturing and packaging a semi-rigid acoustic coupling medium (SACM), also referred to herein as a semi-rigid acoustic couplant (SAC) that provides an acoustic coupling medium for ultrasound diagnostic and treatment techniques. The methods in accordance with the embodiments disclosed herein include scalable, cost-effective, and rapid production techniques that can enable mass production of SACMs directly in a packaging ready for immediate use as an acoustic coupling medium, for direct shipment, and/or for long-term storage for later use. For example, the disclosed methods can minimize production surplus and be employable for just-in-time (JIT) operations. In some embodiments, the SACMs can include a hydrogel material to create a semi-rigid hydrogel interface pad, referred to as a "HIP" or "SHIP". The disclosed SACMs offer advantages over conventional coupling mediums such as water baths and standoffs like water bags and puck or sheet hydrogels, e.g., including, but not limited to, offering superior acoustic and mechanical properties.

In some aspects, the disclosed SACMs include an engineered polymer network having the ability to form elaborate geometries and entrap water to a high percentage (e.g., 85% or greater) that provides acoustic impedance matching between ultrasound transducer elements and the target biological volume. The disclosed SACMs are semi-flexible, -stretchable and -bendable, for example, while also being semi-stiff, e.g., analogous to a bendable rubber. In some embodiments, the semi-flexible SACM is stiffer than a soft elastomer, but soft enough to stretch and bend considerably without breaking. The disclosed SACMs provide additional advantages in their manner of manufacture, distribution and application based on their low-cost of fabrication, simultaneous step of sterilization and curing, stable storage, and biocompatibility.

In some embodiments, a SACM article or acoustic probe devices incorporating a SACM in accordance with the present technology are operable to propagate acoustic signals with an acoustic impedance matching of 10 MRayls or less (e.g., more preferably 4 MRayls or less for certain applications, and capable of 2 MRayls or less or 1.6 MRayls or less). In such devices, the SACM conforms to the surfaces of both an acoustic probe device having one or more transducer elements and receiving body (having the target biological volume) based on its semi-rigidity, including a stretchability of 10% to 1000% elongation or greater, e.g., 2500%, compression of 20% to 99.99%, and a Young's modulus of 30 kPa to 500 kPa, or in some embodiments lower than 30 kPa, e.g., as low as 1 kPa.

Example Embodiments of a Semi-Rigid Acoustic Couplant

In some embodiments in accordance with the present technology, a semi-rigid acoustic coupling medium (SACM) includes a monomer, a polymer (e.g., a block copolymer), a dispersive phase, a covalent crosslinker agent, cationic crosslinking agent, catalyst, and/or a free radical initiator.

A function of the monomer is to serve as the primary, structural network for the hydrogel. In some embodiments, the monomer is an acrylamide. Non-limiting examples of acrylamide monomers include dimethylacrylamide (DMA), diethylacrylamide (DEAA), phenyl acrylamide, tert-butylacrylamide, octadecylacrylamide, isopropylacrylamide, or diphenylmethylacrylamide. The monomer is sometimes referred to as the "1° network". In some embodiments, for example, the 1° network monomer includes DMA.

A function of the polymer is to provide a secondary, grafted sacrificial network for the hydrogel. In some embodiments, the polymer is a polysaccharide. Non-limiting examples of polysaccharides include sodium alginate (SA), potassium alginate, calcium alginate, ammonium alginate, low acetylated gellan gum, high acetylated gellan gum, modified starches, agar, k-Carrageenan, l-Carrageenan, low methoxy pectin, high methoxy pectin, methyl cellulose, hydroxypropyl methyl cellulose, cellulose/gelatin, or propylene glycol alginate. The polymer is sometimes referred to as the "2° network". In some embodiments, for example, the polymer is composed of a SA block copolymer. In some embodiments, the polymer is a block copolymer, which can be referred to as the "2° network" with respect to the disclosed articles and methods for producing a semi-rigid acoustic coupling medium. In some embodiments, for example, the block copolymer is an alginate, such as the SA block copolymer.

In some embodiments, the dispersive phase is water (e.g., deionized water (DI $H_2O$)), which can be present in an amount of about 75.65 wt % to about 95.98 wt % of the total weight of the hydrogel interface pad.

In some embodiments, the covalent crosslinker agent is an acrylamide. Non-limiting examples of acrylamide covalent crosslinkers include N',N'-methylene bisacrylamide (MBA), bisacrylamide, ethylene bisacrylamide, piperazine diacrylamide, or ethylene glycol bisacrylamide. The covalent crosslinker agent is sometimes referred to as the 1° network crosslinker. In some embodiments, for example, the 1° network crosslinker includes MBA.

In some embodiments, the cationic crosslinking agent is a monovalent, divalent, trivalent metal. For example, a cationic crosslinking agent can be a transition metal, an alkali metal, or an alkaline earth metal where the metal is the $1^+$, $2^+$, or $3^+$ oxidation state. In some embodiments, the cationic crosslinking agent is lithium, sodium, potassium, magnesium, calcium, zinc, zirconium, iron, cobalt, nickel, titanium, or copper. In some embodiments, the cationic crosslinking agent is in the form of any monovalent divalent, or trivalent salt. For example, in some embodiments the cationic crosslinking agent is any sulfate, phosphate, chloride, bromide, triflate, amine, or carboxylate salt. In some embodiments, the cationic crosslinking agent is calcium sulfate (CA), calcium phosphate, calcium chloride, calcium bromide, or calcium triflate. The cationic crosslinking agent is sometimes referred to as the 2° network activator. In some embodiments, for example, the 2° network activator includes CA.

A function of the catalyst is to promote and/or increase the rate of the chemical reaction that forms the hydrogel composition. In some embodiments, the catalyst is an amine. Non-limiting examples of amine catalyst include aliphatic amines, N',N',N,N-tetramethylethylenediamine (TMED), benzyldimethylamine, methylamine, or triethyl amine.

A function of the free radical initiator is to generate free radicals that initiate the formation of the hydrogel polymer network. Non-limiting examples of free radical initiators includes ammonium persulfate (APS), peroxides such as dialkyl peroxides, hydroperoxides, diacyl periods, or azo-compounds (i.e., —N═N— moieties). In some embodiments, the initiator is a photoinitiator. Non-limiting examples of photo initiators include ribofalvin-5'-phosphate, ribofalvin-5'-phosphate sodium, ethyl (2,4,5-trimethylbenzoyl) phenyl phosphinate (TPO-L), bis-acylphosphine oxide (BAPO), 2-hydroxy-2-methyl propiophenone, methylbenzoyl formate, isoamyl 4-(dimethylamino) benzoate, 2-ethyl hexyl-4-(dimethylamino) benzoate, or diphenyl(2,4,6-trimethylbenzoyl) phosphine oxide (TPO). Additional, non-limiting examples of suitable photo-initiators include 1-hydroxycyclohexyl phenyl ketone (Irgacure 184), 2,2-dimethoxy-2-phenylacetophenone (Irgacure 651), and 2-methyl-1-[4-(methylthio) phenyl]-2-(4-morpholinyl)-1-propanone (Irgacure 907), hydroxyacetophenone, phosphineoxide, benzophenone, and lithium phenyl-2,4,6-trimethylbenzoylphosphinate (LAP). The free radical initiator is sometimes referred to as the 1° network activator. In some embodiments, for example, the 1° network activator includes TMED In some exemplary embodiments of the present disclosure, a semi-rigid hydrogel interface pad is made up of two water soluble polymer networks: a primary (1° network) scaffold and a secondary (2° network) sacrificial graft. In some embodiments, the hydrogel interface pad includes a dimethyl acrylamide monomer (DMAm), a sodium alginate block copolymer (P(SA)), and water. For example, the DMA concentration can be engineered to affect the elasticity and conformability. In some embodiments, the hydrogel interface pad further comprises MBA, TMED, CA, and APS.

Example Methods for Fabricating SAC Compositions and Articles

Example embodiments of a method for scalable, cost-effective, and rapid fabrication of semi-rigid acoustic couplants are described, which in some embodiments, can produce SACMs directly in a packaging ready for immediate use as an acoustic coupling medium, for direct shipment, and/or for long-term storage for later use. The chemical and morphological characteristics of semi-rigid acoustic coupling medium as disclosed herein are not only dependent on the chemical constituents, but also on the physical interactions within the medium, at mold-solution interfaces, and a host of other phenomena. Thus, the way SACMs are fabricated and packaged adds additional layers of complexity to manufacturing.

Figure 3:
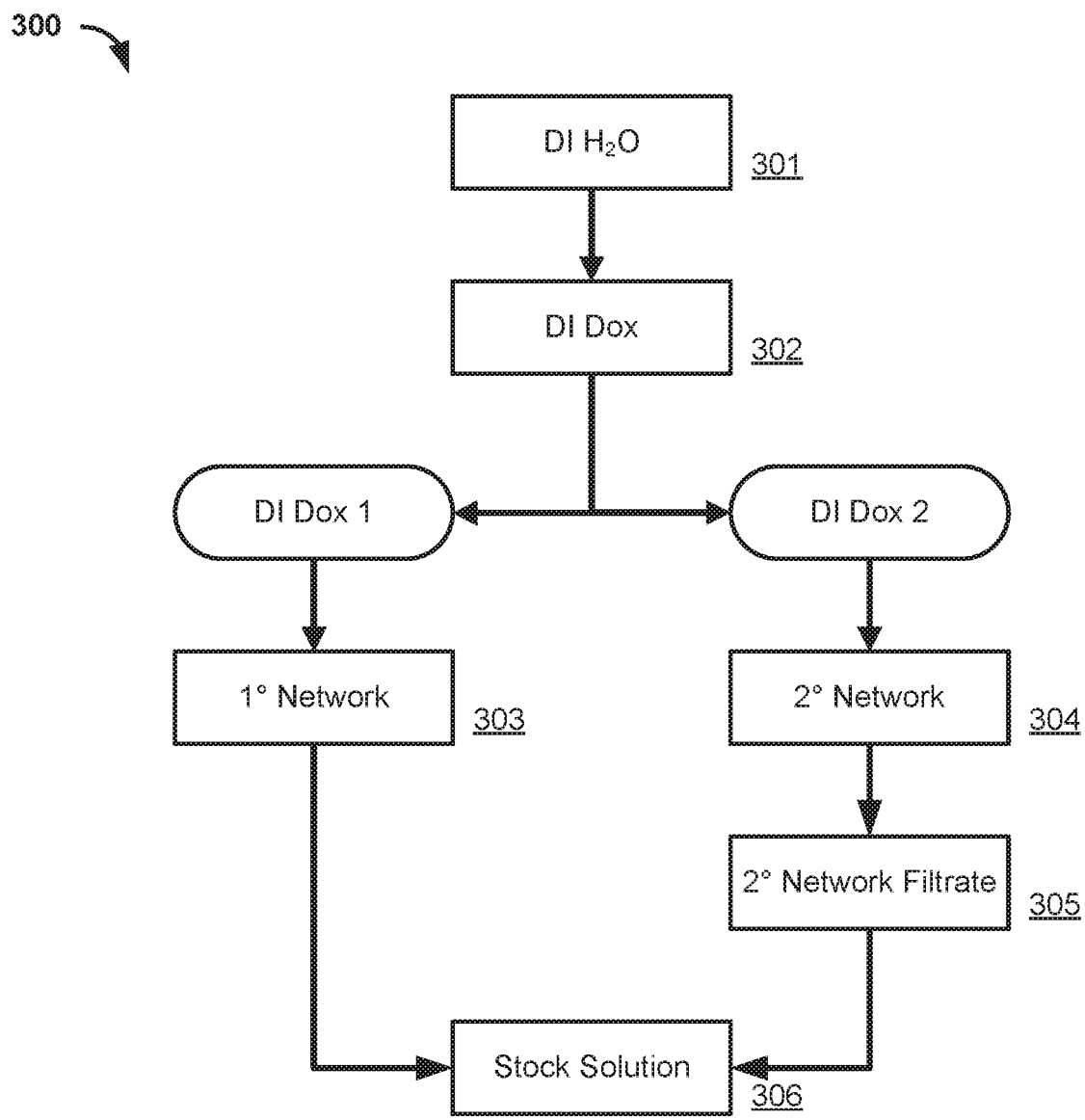
FIG. 3 shows a diagram depicting an example embodiment of a method for preparing a stock solution for fabricating a semi-rigid acoustic coupling medium (SACM) in accordance with the present technology.

FIG. 3 shows an example embodiment of a method for producing a stock solution in preparation for fabricating the SACM in accordance with the present technology. The exemplary method, labeled 300, includes a process 301 to remove exogenous oxygen from deionized water (DI $H_2O$), e.g., by sparging the DI $H_2O$ with an inert gas (e.g., Ar, $N_2$, He, etc.) to produce and/or procure Deionized-Deoxygenated Water (DI-Dox). In some embodiments, the DI $H_2O$ includes Type I or Type II DI $H_2O$. The DI-Dox is essential, otherwise unwanted side reactions, constituent degradation, adventitious contamination, and low extent of polymerization will occur. DI-Dox water is also vital to prevent premature secondary, grafted sacrificial network (i.e., two prime (2°) network), which occurs in the presence of solvated cationic salts at standard temperature and pressure (STP).

Following DI-Dox production, the method 300 includes a process 302 to separate the DI DOX water into two vessels: DI Dox 1 and DI Dox 2. To the first DI-DOX water vessel (DI Dox 1), a monomer to provide the primary, structural network (i.e., 1° network, e.g., such as DMAm) of the stock solution is added at a process 303 of the method 300. Upon dissolution, for example, cooling occurs as the example DMA monomers disperse endothermically throughout the DI Dox 1 solvent. Simultaneously, the method 300 includes a process 304 to disperse a second constituent to provide a secondary, structural network (i.e., 2° network, e.g., such as SA) in the second DI-Dox water vessel (DI Dox 2) at 304, producing a viscous clear, or translucent-amber, solution. Dilute DMAm solutions have observed near-Newtonian behavior while dilute SA solutions exhibit thixotropic shear thinning and pseudoplastic behavior. When mixing SA, it is important to avoid fisheye formation.

Figure 4:
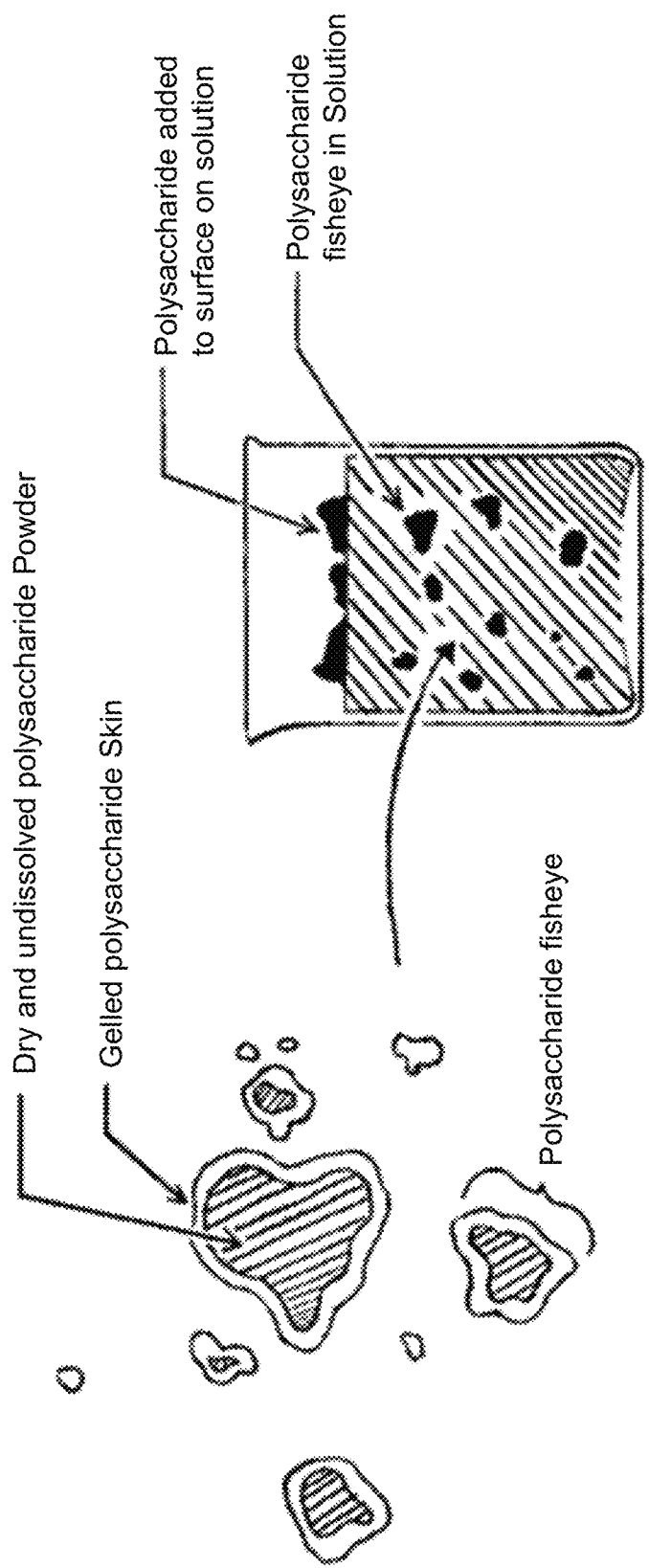
FIG. 4 shows an exemplary diagram depicting the formation of aggregates from soluble polysaccharides.

FIG. 4 shows an exemplary diagram depicting the formation of aggregates, referred to as "fisheyes", from soluble polysaccharides. As shown in FIG. 4, fisheye formation occurs when soluble polysaccharides form aggregates coated in gelled polysaccharide "skin" around dry, undissolved polysaccharide powder, impeding solvent penetration and polysaccharide dispersion, and are notoriously difficult to solvate even at high temperatures (e.g., ≤98° C.). If not removed or dissolved, these clumps will interfere with acoustic transmission, distorting VOIs in US images; entrain air in the skin layer, generating US images with comet like bright spots and an obscuring, opaque tails; generate localized, brittle stress regions filled with undissolved polysaccharide; and, affect the bulk and surface composition of the material which effects the material morphology, conformability, and biocompatibility.

Referring back to FIG. 3, the method includes a process 305 to filter the 2° network. For example, once the 2° network is dissolved in DI Dox 2, the example SA solution is filtered to remove lurking fisheyes. The method 300 includes a process 306 to produce a stock solution for fabricating a SAC by adding the 1° network solution (e.g., DMAm solution) to the resulting filtrate (i.e., 2° network filtrate) from the 2° network solution (e.g., SA solution) under an inert atmosphere. The resulting combination solution of the 1° network and 2° network filtrate solutions (e.g., DMAm and SA) serves as a separate admixture, or "stock solution." The resulting stock solution is voluminous and therefore is stable (e.g., >30 min).

Notably, from the stock solution, small batches of SACMs can be manufactured when needed; thus, surplus inventory is minimized, materials consumption decrease, waste is mitigated, and the overall Cost of Manufacturing (COM) is cut. Additionally, Fixed Capital Investment (FCI) and equipment maintenance are minimized by reducing the number of unit operations while increasing the process streams flexibility to produce a variety of SACM geometries, and acoustic and mechanical properties—achieved by changing the Dispensed Aliquot Volume (DAV) and the mold for the forming the SACM in a desired geometry, size and shape (e.g., such as a tray type), and the composition of the small batch respectively. Tray type refers to the mold used to manufacture the SACMs which enables curing, provides environmental protection, cleanliness, and/or sterility of the resulting SACM. As such, the tray serves a significant component of both the manufacturing and distribution process.

Figure 5:
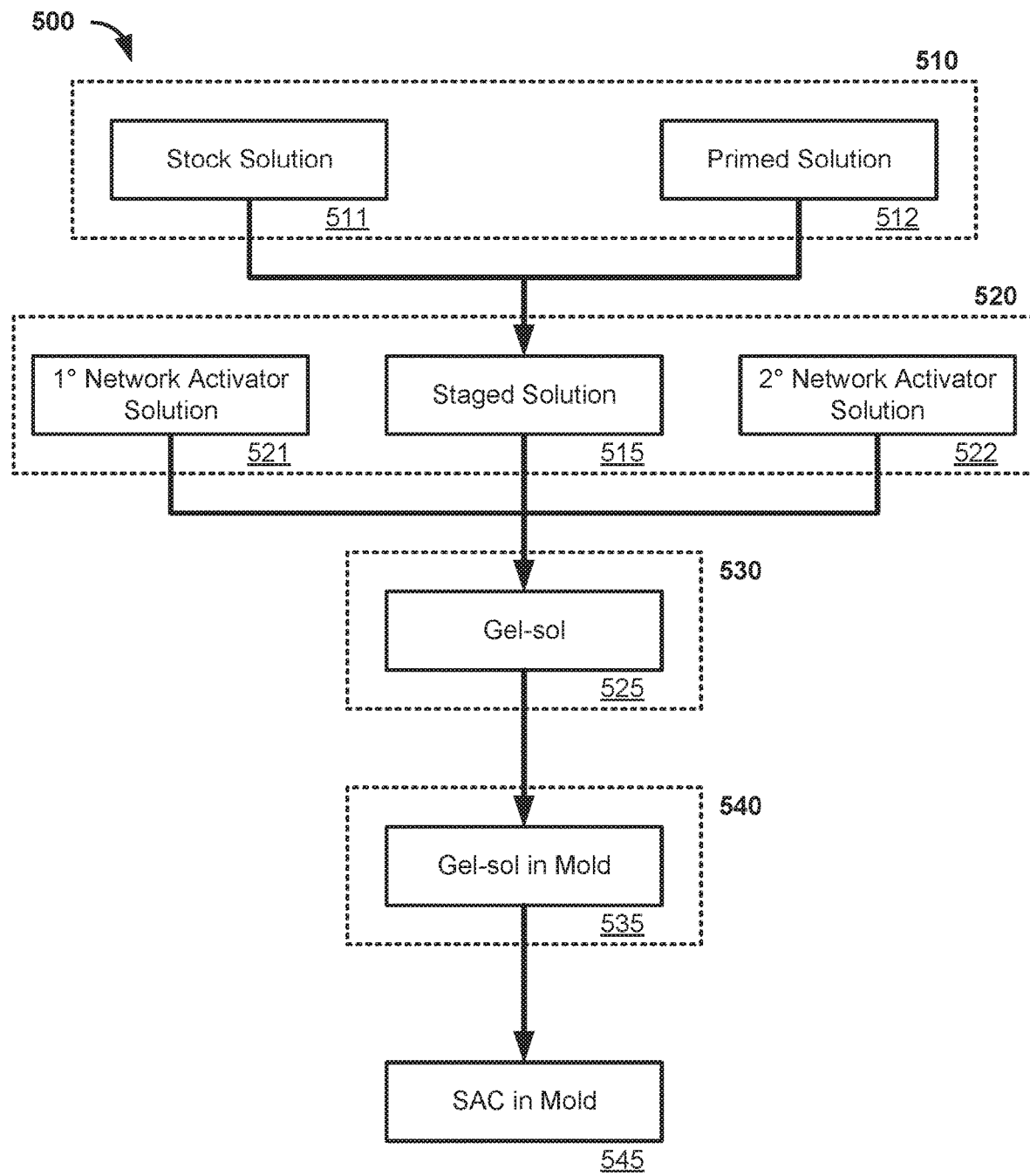
FIG. 5 shows a schematic depicting an example embodiment of a method for fabricating a SACM in accordance with the present technology.

FIG. 5 shows an example embodiment of a method for producing a SACM in accordance with the present technology, labeled 500. The method 500 includes a process 510 to provide or prepare a stock solution 511, which includes a monomer (e.g., the 1° network component) and a block copolymer (e.g., the 2° network component) in deoxygenated water, and to provide or prepare a primed solution 512, which includes a covalent crosslinking agent (e.g., the 1° network crosslinking agent) and a catalyst. In some implementations of the method 500, for example, the process 510 includes using the stock solution produced by the method 300. The process 510 includes producing a staged solution 515 by adding the stock solution 511 and the primed solution 512 together. The method 500 includes a process 520 mixing the staged solution 515 with a solution 521 comprising a monomer activator (e.g., the 1° network activator) and a solution 522 comprising a block copolymer activator (e.g., the 2° network activator) to form a gel-sol 525. In some implementations, the gel-sol is a suspension of gelling corpuscles that are close to a state in which corpuscles would amalgamate and form a continuous, 3D polymer network making up the SAC. The method 500 includes a process 530 to dispense the gel-sol 525 into a mold, thereby producing a molded gel-sol 535 in a shape, size and/or geometry desired for a semi-rigid acoustic couplant. The method 500 includes a process 540 to cure the molded gel-sol 535, in the mold, to form the semi-rigid acoustic couplant 545. In implementations of the method 500, the method 500 is carried out in an inert atmosphere. In some implementations, the method 500 includes sterilizing the gel-sol by applying radiation (e.g., X-ray, γ-ray, UV or other).

The method 500 can be implemented on-demand or just-in-time. For example, when a batch of SACMs are ordered, the stock solution 511 is added to a smaller vessel and degassed to remove air entrained during transport. Agitated, the stock solution 511 is sparged and blanketed with inert gas (e.g., $N_2$, He, Ar, etc.) under vacuum (e.g., −15 inHg gauge) and elevated temperature (e.g., 50° C.), reducing the solution viscosity to flash-out gaseous oxygen and inert gas bubbles. Ensued sparging ensures Dissolved Oxygen (DO) is less than or equal to the minimum DO (e.g., $DO_{min}$=0.1 ppm). Oxygen quenches free radical initiation, degrades the catalyst, and obstructs efficient propagation, leading to excessive residual monomer (e.g., >0.03 ppm DMAm) remaining in the SACM, which is a toxic, possibly carcinogenic, irritant. Once oxygen is removed, the solution is cooled back to room temperature under an inert atmosphere before proceeding to the next series of processing steps.

In some implementations of the process 510, e.g., to prepare the primed solution 512, in a separate vessel, the 1° network crosslinking agent (e.g., MBA) and the catalyst (e.g., TMED) are dissolved in DI-DOX water under an inert atmosphere to make a "primed" admixture. The primed solution 512 is then fed into the stock solution to generate the "staged" solution. In some implementations of the process 520, for example, the staged solution 515 is capable of crosslinking immediately once both the 1° network activator (e.g., APS) and the 2° network activator (e.g., CA) are added to the staged solution. For example, because oxidation of TMED vitiates rapidly in aqueous mediums with DO, the staged solution cannot be stored for long durations like the stock solution, otherwise variable reaction rates will generate SACMs with variegated mechanical, acoustic and biocompatibility characteristics.

While mixing the staged solution, both the 1° network activator (e.g., APS) and 2° network activator (e.g., CA) solutions are formulated by dissolving the example constituents APS and CA in DI-DOX water, respectively. In some implementations, for example, both the 1° network activator and 2° network activator solutions are simultaneously fed into the staged solution 515 at the process 520 to produce a homogenous APS and CA dispersion, the gel-sol 525. Failure to do so can create reaction hotspots, resulting in SACMs with variable mechanical, acoustic, and biocompatibility characteristics per a single batch.

DMAm polymerization is exothermic and must be controlled to prevent a runaway reaction. For example, a runaway reaction occurs where heat generated from polymerizing and grafting increases the temperature of the solution, increasing the rate of reaction, and further increasing the temperature; thus, a positive feedback loop can be generated. Consequently, uncontrolled reactions generate extremely short 1° crosslinks that are unable to stretch and distribute forces under load, yielding a SACMs with low fracture toughness. Excessive heat can also degrade the P(SA) block copolymers as the solution increases in temperature (e.g., >75° C.), and warp the plastic packaging when dispensed into polyethylene terephthalate glycol (PETG) trays. Worst case scenarios can lead to premature gelling in the vessel, degradation of the final product, and a possible explosion from rapid temperature and pressure buildup.

Preventing critical failures requires excellent process control. Heat generated from the reaction can be removed via convective heat exchange and varying the agitation rate. Quenching agents, like monomethyl ether of hydroquinone (MEHQ), can also be added lower the rate of reaction and prevent a positive feedback loop from occurring. However, copious MEHQ, or other retarder, can also increase the amount of residual monomer and might impede effective 1° network crosslinking, yielding brittle and rigid SACMs. Reducing the batch volume also reduces the amount of reacting mass, reducing the risk and severity of a runaway reaction and improving heat exchange. Furthermore, as the amount of initiator and monomer increase, the rate of reaction increases, producing more heat as the number of effective number of polymerization reactions increase. As a result, adjusting the flow rate and temperature of added initiator, and the temperature and agitation rate of the staged solution, will control the amount of heat released. For example, slowly adding cold initiator to a cool, moderately agitated solution reduces the rate of heat generated while rapidly adding hot initiator to warm, vigorously agitated solution increases the rate of heat generated.

In some implementations of the method 500, for example, when both the 1° network activator and 2° network activator solutions are completely dispensed into the stage solution, the "gel-sol" is formed, which must be completely dispensed from the vessel before the potlife of 30 min is exceeded. In some embodiments, the resulting gel-sol 525 exhibits liquidity for long durations (e.g., has an increased pot-life). Liquidity refers to the viscosity of the gel-sol and by exhibiting liquidity, the gel-sol 525 maintains the characteristics of a liquid. Excessive crosslinking can suppress the liquidity of the gel-sol 525. Controlling the rate of reaction changes the duration the gel-sol remains as a liquid/suspension before crosslinking into a semi-solid hydrogel, or before the polymerizing gel-sol becomes too viscous to cast into a mold without the inclusion of air bubbles. Thus, the liquidity has important implications for large-scale and small-scale manufacture of hydrogel pads. For example, to minimize the formation of bubbles (e.g., micro-bubbles) that can become captured (e.g., "locked") within the semi-solid hydrogel matrix, a challenge frequently encountered in hydrogel fabrication, the gel sol liquidity—when the gel-sol viscosity is low—can be prolonged by retarding and/or post-polymerizing the gel-solution 525. Notably, a failure to remove and/or prevent bubble formation can result in SACMs with properties associated with poor acoustic transmission. For example, the resulting SACMs with captured bubbles in the hydrogel matrix can have reduced acoustic performance due to increased attenuation, unwanted scattering, and/or obscured ultrasound images. Additionally, bubbles entrapped within the hydrogel matrix also compromise the mechanical properties of the SACMs, resulting in increased localized stress regions as well as a decreased elasticity and/or conformability.

Potlife further controls the batch size and the length of time before the gel-sol sets/gels. Gel-sol with a long potlife can yield large SAC batches while gel-sol with a short potlife can only be produced in small batches. The batch size is also dependent on the stepwise flow rate of gel-sol dispensed from the vessel into a tray/mould which is calculated from the rate of DAV per tray, DAV flow rate, and tray velocity. For example, if the stepwise flow rate is too low, then the gel-sol will exothermically gel inside the batch, rapidly increasing the pressure and temperature inside the vessel. Despite a relatively long potlife, small batch vessels (e.g., ≤150 L) are used instead of large batch vessels (e.g., >150 L) to mitigate the risks and severity of critical failures by increasing effective heat exchange (e.g., vessel surface area to gel-sol volume ratio), improving homogenous mixing, and reducing the amount of polymerizing mass. Small batches are also easier to degas, simpler to maintain, and less arduous to Clean in Place (CLIP), for example.

In some implementations of the process 530, the viscous gel-sol 525 is dispensed into molds (e.g., PETG trays) under a blanket of inert gas to prevent oxygen diffusion into the medium which can create cure gradients in the material as a function of thickness. The tray is made of vacuum formed, PETG which is UV, ion-beam, and γ-ray transparent, useful if sterilization and UV curing are desired, in which case photoinitiator is added to the 1° network activator (e.g., APS) solution before casting/dispensing. For example, PETG trays have high surface energy, which reduces the amount of oxygen trapped between the gel-sol and the tray wall during curing. If a low surface energy, or unwettable surface, material is used, then there is greater risk of oxygen adsorption and entrapment on the packaging surface, creating a significant curing gradient (e.g., ≥1 mm thick).

In some implementations, PETG trays are manufactured by first bead blasting extruded sheets of plastic to roughen the surface to vacate air when the plastic is pulled against a male or female mold, preventing wrinkling and creasing during suction. Then, a sheet of PETG plastic is then clamped over a sealed window in a class 100,000 clean room and heated past the glass transition temperature (To but below the melting temperature (Tm), making the plastic pliable enough to conform to the mold surface, but not too soft where it will excessively thin or rip. Molds with steep drafts and undercuts require positive pressure, vacuum snap-back, and/or plug-assists to conform the plastic against the positive or negative mold. Cooled, the trays are then guillotined, and double-bagged afore shipment.

Once vacuum formed and shipped, PETG trays are "denested"—removed from one another when stacked. If PETG trays do not have denest features, then the trays may stick to one another during production, affecting SACM processing downstream. Features include permeating silicones or other lubricants after plastic extrusion or vacuum forming, and/or inorganic fillers like talcum or mica that break up the smooth surface to reduce the amount of contacting surface area between each tray. Illustrations for lubricating skin layers and slip-features are presented in FIGS. 6 and 7, respectively.

Figure 6:
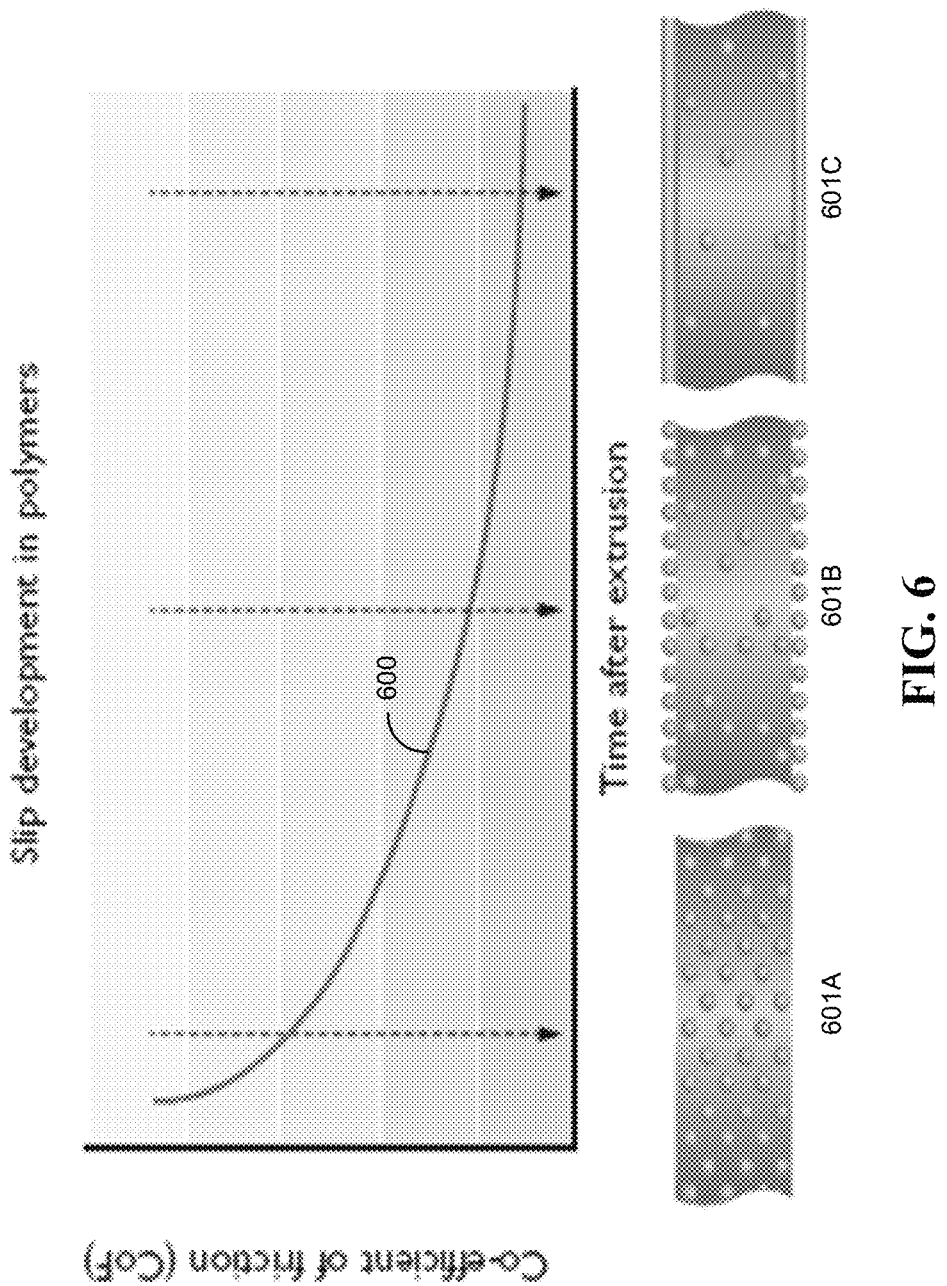
FIGS. 6 and 7 show a diagram and images of lubricating skin layers and slip-features, respectively, for polyethylene terephthalate glycol (PETG) trays in an example embodiment of a fabricated SACM.

FIG. 6 includes a plot 600 demonstrates how the coefficient of friction decreases for the surface of the PETG trays, as the time after extrusion increases. Beneath the plot 600 are illustrations of PETG trays referred to as 601A, 601B, and 601C that depict the lubricating skin layers with features that decrease the coefficient of friction from left to right. 601A illustrates how the lubricant remains in the plastic shortly after the plastic was extruded, injection molded, or vacuum formed into a tray. After some time, the lubricant in the plastic, starts to exude out of the plastic, developing a film of lubricant on the outer surface of the plastic as shown in 601B. Eventually, the lubricant secreted from the plastic forms a continuous film of lubricant across the entire plastic part, with some residual lubricant remaining in the plastic as seen in 601C.

Figure 7:
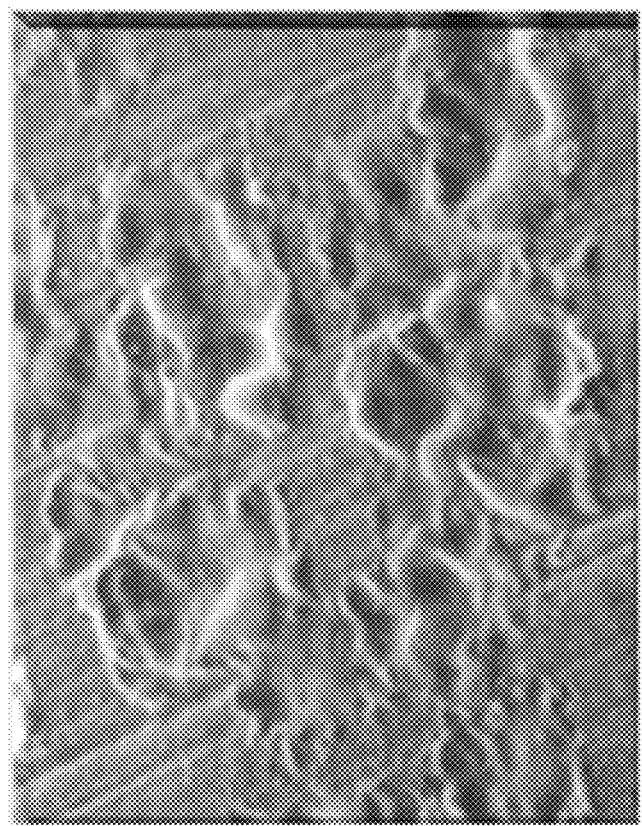
Figure 7:
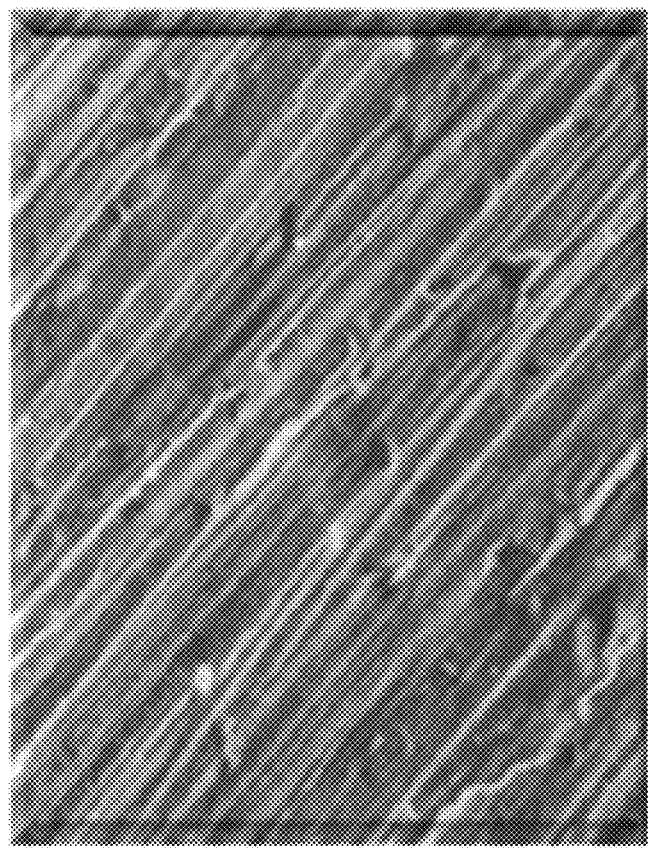

FIG. 7 shows images of slip-features for PETG trays in an example embodiment of a fabricated SACM. While FIG. 7 shows an exemplary embodiment of the tray comprised of PETG, the tray can be comprised of other plastics not limited to PETG. For example, non-limiting examples of suitable materials for the mold container (e.g., used in the process 540) include acrylonitrile butadiene styrene (ABS), polyethylene terephthalate (PETE or PET), polyethylene terephthalate (APET), polycarbonate (PC), polyethylene (PE), polypropylene (PP), polystyrene (PS), cross-linked polyethylene (XLPE), and thermoplastic polyurethane (TPU).

Table 1 describes example categories of techniques for preparing and/or properties of example materials that can be suitable for fabrication of the mold (e.g., tray).

TABLE 1

| Category | Value(s) |
|---|---|
| Sterilization | EtO, γ, EBI, UV, Plasma Gas |
| Curing/Gelling | Redox, γ, EBI, UV, Heat |
| Manufacturing Method | Vacuum Forming, Injection Molding |
| Compliance | ISO 10993 |
| Void of: | BPA, Chlorine, and other Water Leachables |
| Thickness (mil) | 5-60 |
| Density (g/cc) | 0.90-2.00 |
| Haze (%) | 0.0-1.0% |
| Refractive Index | 1-2 |
| Yield Strength (MPa) | 35-85 |
| E (MPA) | 1000-2100 MPA |
| Water Permeation (g/m$^2$ · 24 hrs) | 0-10 |
| Water Absorption @STP for 24 hrs (%) | 0.0-0.8 |
| Oxygen Permeation (cc · mm/m$^2$ · 24 hrs · atm) | 0-10 |
| Contact Angle of Water @ STP (degrees) | 0-90 |
| Surface Energy @ STP (dyne) | 30-90 |
| Coeff. Friction | 0.05-1.20 |
| Blocking Force (N) | 0.50-5.00 |
| Glass Transition Temperature (° C.) | >80 |
| Melting Temperature (° C.) | >140 |
| Linear Thermal Expansion (μm/m · K) | <80 |
| Heat Deflection Temperature (° C.) | 70-80 |

In some implementations, the mold includes a plastic or a metal. In some examples, the plastic mold includes a thermally-formed plastic, an injection-molded plastic, a casted plastic, or a machined plastic. In some examples, the metallic mold includes a thermally-formed metal, an injection-molded metal, a casted metal, or a machined or drawn metal. PETG is one example of the plastics suitable for SAC manufacturing. Other amorphous, crystalline, and semi-crystalline elastomers, thermosets, or thermoplastics materials, e.g., ABSs, PETEs (PET), PEITs, PCs, PEs, PPs, PSs, XLPEs, HIPSs, Nylons, PUs, Silicones, TPUs, TPCs, and TPEs, are also suitable if certain conditions and parameters are met, e.g., such as those listed in Table 1. In some implementations, the mold can include a passivated or coated metal or metals meeting conditions and parameters like those in Table 1.

In some embodiments, the packaging for the SACM provides a sterile barrier against microbes, maintains the moisture of the SACM, and serves as the SACM mold. In some implementations, by combining the packaging and the mold (e.g., the PETG tray), the number of unit operations required can be reduced and the sanitation of the final product can be improved while simultaneously reducing the product cost and Turn Around Time (TAT).

In some implementations, the tray is comprised of a cost effective, sterile, and low oxygen adsorption packaging material such as a thermoplastic that has thermal stability, resists chemical attack (e.g., combination reactions, decomposition reactions, and/or combustion reactions, polymerization reactions) and/or endures radiological environments, and has a high surface energy coating. In some implementations, for example, the trays are rigid enough that once formed, they do not warp and bend at elevated temperatures when dispensing, gelling, and post curing the SACM. In some implementations, for example, the trays have a Heat Deflection Temperature (HDT) that is low enough such that the HDT that does not prohibit injection molding and vacuum thermoforming.

Another important consideration for the tray includes oxygen permeability. In some implementations, for example, the tray must allow for a controlled oxygen environment to minimize oxygen exposure in order to prevent quenching of free radical polymerization, which can generate residual monomer concentration gradients. Accordingly, in some implementations, the oxygen permeation through the packaging must be slower than the time to fully cure the SACM. In some implementations, the tray includes a material (e.g., like PETG) that minimizes water absorption and permeation and prevents embrittlement and excessive SACM swelling.

Blocking force, or the retaining force exerted by intramolecular attractions between the trays, and the coefficient of friction for stacked trays is an important consideration to minimize trays with high surface energy from sticking, otherwise the trays can become "glued" together. Non-stick features should be inert, non-toxic, and non-irritating to meet biocompatibility requirements. In some implementations, the trays are transparent to allow for observation of the SACM curing progress and to check for air bubbles during QA.

In some implementations of the method 500, while setting (potting, gelling) and/or sterilizing, the gelling SACM can be sealed in an inert atmosphere with an aluminum foil cover, or other metallic or plastic cover, for anti-tampering, microbe-barrier, and storage purposes. Once sealed, an additional retainer lid snap-fits on the tray to retain the foil seal and curing hydrogel. SACMs can have a dwell time (e.g., 8 hr), or "green" time, after potting before the specified mechanical and acoustic properties are developed. While green, SA grafts and networks orient themselves in the lowest energy conformation by forming ion-ion junctions around the divalent CA ions. Simultaneously, a UV post-cure can be implemented during the green stage to increases the extent of polymerization, significantly reducing the amount of residual monomer remaining via additional cross-linking and shortening the dwell time. After dwelling, the fully cured SACMs are packaged and shipped in non-transparent containers to prevent lysis of P(DMAm) which occurs after the green stage in direct UV-radiation.

The example SACMs described herein can be cured using numerous curing methods. Non-limiting examples of curing methods include redox-curing methods, radiation-curing methods, and/or thermo-curing methods.

Example Redox-Curing Methods

In some implementations, redox initiators such as lyse when dissolved in aqueous solution can, when promoted by a catalyst, initiate DMAm vinyl addition polymerization. For example, TMED catalyzes APS lysing into a bisulfate and a sulfate-radical, which is stable over a broad set of temperatures (e.g., 5-110° C.) and pH levels (e.g., 7-10 pH) ranges. In some implementations, the sulfate-radicals fully react to give bisulfate as a side product which has some effect on echinoderms such starfish, sea-cucumbers, crinoids, etc. but significantly, have zero impact on mammals. In some implementations, longer reaction times yield SACMs with long kinetic chain lengths on average, providing stretchy, strong, and pliable SACMs.

In some implementations, the example methods of manufacturing redox-initiated SACMs require less equipment, and therefore, an overall reduction in equipment costs and maintenance costs. For example, issues regarding solution viscosity can be mitigated because initiation occurs during agitation, improving initiator free radical diffusion and motility in the gel-sol, generating more successful free radical initiator collisions with the vinyl group on DMAm. Availability and low cost of most pharmaceutical and reagent grade redox-initiators for biomedical applications are important for JIT manufacturing.

Example Radiation-Curing Methods

In some implementations, methods of the present disclosure, use irradiation-initiation to manufacture the SACM to begin vinyl addition polymerization. Unlike a redox-initiated reaction, UV, Electron-Beam irradiation (EBI), and gamma ($\gamma$) radiation-initiated reactions do not begin polymerizing the gel-sol until incident radiation exposure. For UV initiated reactions, a UV emitter, like a high-pressure or low-pressure mercury lamp, radiates UV light at the target. The distance, frequency, intensity, and placement beneath the emitter determines the fluence rate (J/s)—flux-rate of incident UV light a given distance from the emitter and of a known emitter length—used to calculate the Dosage (J)—the amount of energy absorbed by the gel-sol. Fluence rate and the total dose will determine the gel time—the time it takes for the gel-sol to gel—and the mechanical, acoustic, and biocompatibility characteristics. In some implementations, UV-curing requires a photoinitiator that can absorb UV-light at a frequency not absorbed by other constituents which will lyse or sacrifice an alkene or alkyne to form a free radical. Once formed, radicalized photoinitiators rapidly initiate the reaction, using up almost all of the photoinitiator before gelation.

In some implementations of $\gamma$ radiation-initiated reactions, initiation reactions induced by $\gamma$-radiation do not need an initiator since $\gamma$-radiation lyses water molecules into reactive hydroxide radicals, as process also known as radiolysis, which readily initiate vinyl addition polymerization. The process can eliminate the need for initiators and cross-linkers. In some implementations, the SACM mechanical characteristics are dependent on the dose (e.g., J/kg or Gy). Dose can be controlled by varying the gel-sol exposure to an isotope of cobalt, cobalt-60 ($^{60}Co$), or other, by varying the intensity that is e.g., adjusting the lead aperture/shutter and duration of exposure, for example. Unlike most materials, water readily absorbs $\gamma$-rays, initiating vinyl addition polymerization homogenously throughout the bulk of the gel-sol.

In example implementations using EBI radiation curing, EBI is generated from an ionizing source composed of an emitter (e.g., cathode), grid (e.g., bias cup), and anode which make up the ion gun and high voltage field. The concentrated beam of electrons is accelerated through a magnetic field, focused using a magnetic focusing lens focusing or spreading the ionizing radiation while a magnetic deflection coil steers the ionizing radiation. Unlike $\gamma$-irradiation which knocks an electron loose when occasionally colliding with an atom, EBI directly bombards the gel-sol with a beam of electrons, generating for example, hydroxyl free radicals and DMAm free radicals, which can promote crosslinking without an initiator or crosslinker. In some implementations, the $\beta$-radiation is more interactive with the gel-sol and therefore, the thickness of the SAC needs to be accounted for when crosslinking the entire gel-sol. EBI dosage is similar to the $\gamma$-ray dosage (Gy) but is dependent on more factors: the energy of ionizing radiation (expressed in keV or MeV), the intensity of ionizing radiation (number of bombarding electrons), ion-acceleration and speed, and exposure time. Control over the dosage parameters can be exercised with EBI, significantly reducing the exposure time from minutes to seconds. Directional and focusing control also give EBI processes discrete crosslinking capabilities, crosslinking areas of the gel-sol more than others to create a functionally graded material.

In some implementations using either EBI or γ-irradiation, the methods may not include a chemical initiator or crosslinker and can ameliorate issues regarding the gel-sol viscosity's impact on the frequency factor. Dosimeters indicate irradiation has been applied and the product is fully crosslinked, giving an extra level of quality assurance. In some implementations, SACMs crosslinked using EBI or γ-irradiation result in a sterile product, and the methods can provide improved control over the polymerization of the product and mitigate auto-acceleration risks.

the tray without incorporating bubbles, then promptly UV-cured by photoinitiating the excessive photoinitiator under a curtain of inert gas, reducing the gelation time. Once sealed, the SACs can go into a UV-post-cure-oven (e.g., inert atmosphere at <20° C.), which simultaneously sterilizes the packaging and SAC, and extensively decreases residual monomer at the SAC-tray and SAC-foil interfaces, reducing the dwell time (e.g., >8 hr) before the SAC is fully cured. The reduced dwell time and less arduous CLIP procedures improve the process TAT, reducing costly inventory and improving processing flexibility.

Below are Tables 2A and 2B which describe some example advantages associated with various curing techniques, such as UV-radiation, γ radiation, and electron beam irradiation (EBI), which may apply to some implementations of the described methods.

Table 2A describes example advantages associated with UV-Radiation, γ radiation, and EBI Curing Methods.

TABLE 2A

| UV-radiation | γ-radiation | EBI |
|---|---|---|
| Low polymer degradation | No initiators and catalyst needed | No initiators, crosslinkers, and catalyst needed |
| Reduced gelation time and longer potlife | Penetrates easily through plastic | Beam steering and focusing for selective curing |
| Simultaneous sterilization and curing | Absorbed homogenously by water | Less hazards than γ-irradiation |
| Less material, waste, and reaction hazards | Simultaneous curing and sterilization | Simultaneous curing and sterilization |
| Less arduous CLIP procedures and moderate TAT | Less Arduous CLIP procedures and moderate TAT | Short exposure times and excellent reproducibility |
| Relatively low-cost unit operations | No post curing required and decreased inventory | Less arduous CLIP procedures and fastest TAT |
| Decreased dwell time and inventory | Better process control and safer reactions | Less material waste and reaction hazards |
| Low cost maintenance | More compact and less maintenance than EBI units | Better process control and safer reactions |
| | Low RM content and homogenous crosslinking | Low RM and homogenous crosslinking |

UV-crosslinking has many of the same advantages of EBI and γ-irradiation crosslinking methods. For example, bleaching indicators signify sterilization and crosslinking are complete, which can be well controlled and risks of auto-acceleration can be mitigated, for example, by eliminating the redox initiator. Unlike EBI and γ-irradiation, UV-crosslinking degrades polysaccharide constituents by several orders of magnitude less (e.g., 1000× less). In some implementations, the UV crosslinking methods can minimize the production of hazardous waste and operations coupled with dramatically lower fixed capital investment, utility, and can reduce costs associated with the generation of sterile SACMs.

In some implementations, the methods for producing SACMs include a hybrid method which can, for example, combine redox initiation with prolonged UV-post curing, or UV-redox curing. In some implementations, the combination of a slow redox-reaction coupled with a UV post cure produces a SACM with a high polymerization yield without high risk runaway polymerization. In some embodiments of the hybrid method, for example, by incorporating less redox-initiator (e.g., APS) than standalone redox-reactions and adding more photoinitiator (e.g., riboflavin 5'-phosphate (Rib)) than standalone UV-reactions to cooled staged solution (e.g., ≤15° C.) in the batch reactor significantly retards the rate of redox-polymerization and increases the potlife (e.g., >30 min). For example, after slowing mixing the polymerizing gel-sol, the gel-sol is quickly dispensed into Table 2B describes example advantages associated with Redox and Redox-UV with curing methods.

TABLE 2B

| Redox | Redox-UV |
|---|---|
| Lowest material, unit-operation, waste, and capital investment costs | Low material, unit-operation, waste, and capital investment costs |
| Homogenous polymerization | Homogenous polymerization |
| Simplest SAC manufacturing method | Low hazardous waste generation |
| Least amount of hazardous waste | Generates long kinetic chain lengths |
| Generates long kinetic chain lengths | Significantly reduces RM and cure gradients |
| | Reduces gelation time and extends batch potlife |
| | Reduces dwell time and inventory |
| | Simultaneous curing and gelation |

Figure 8:
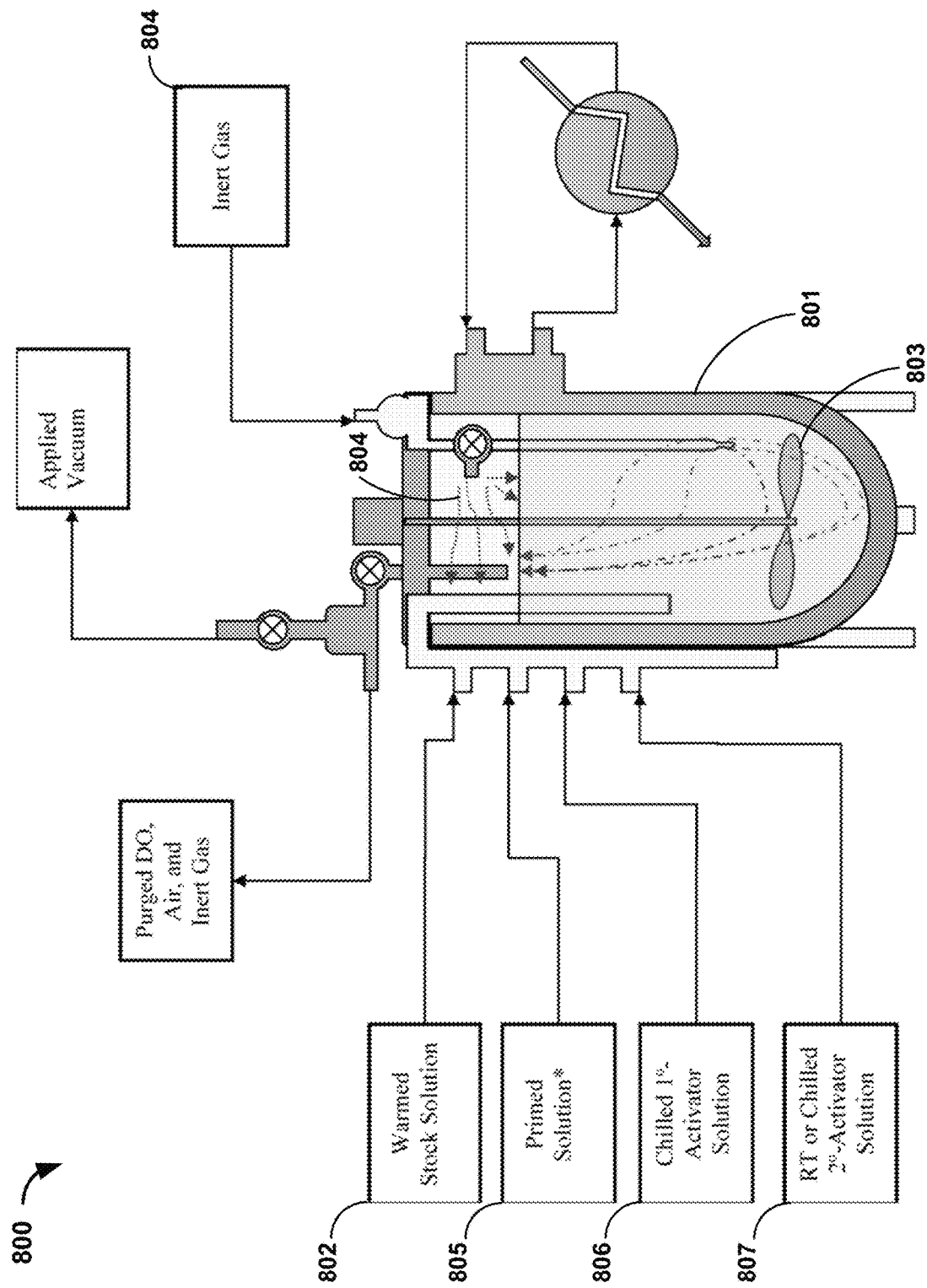
FIG. 8 shows a schematic diagram depicting an example embodiment of a system for fabricating a SACM in accordance with the present technology.

FIG. 8 shows an example embodiment of a system 800 for producing a SACM in accordance with the present technology. In FIG. 8, a stock solution 802 (e.g., SA and DMA dissolved in DI-DOX) is placed in a reactor vessel 801 with a stirring mechanism 803. The stock solution 802 is warmed to lower the viscosity of the solution and then spared with an inert gas 804 until the DO content of the solution is adequate (e.g., $DO_{min}$=0.1 ppm). Next, the stock solution 802 is cooled to room temperature and the primed solution 805 (e.g., TMED and MBA dissolved in DI-DOX water) is added while maintaining the reaction under an inert atmosphere. The addition of the primed solution 805 to the sock solution 802 results in the formation of the staged solution. In an optional step, a photoinitiator is added to the primed solution in order to promote photoinitiated gelation and accelerate UV curing before the primed solution is added to the stock solution. The staged solution is then cooled (e.g., to 15° C.) and a chilled 1° activator solution 806 (e.g., APS dissolved in DI-DOX) and room temperature (e.g., 23° C.) or chilled 2° activator solution 807 (e.g., DA dissolved in DI-DOX) are added in order to initiate the vinyl addition polymerization and 1° and 2° network crosslinking to form the gel-sol. While maintaining the temperature and inert atmosphere of the reactor vessel 801 and the gel-sol, DAVs of the gel-sol are dispensed into PETG trays.

Figure 9:
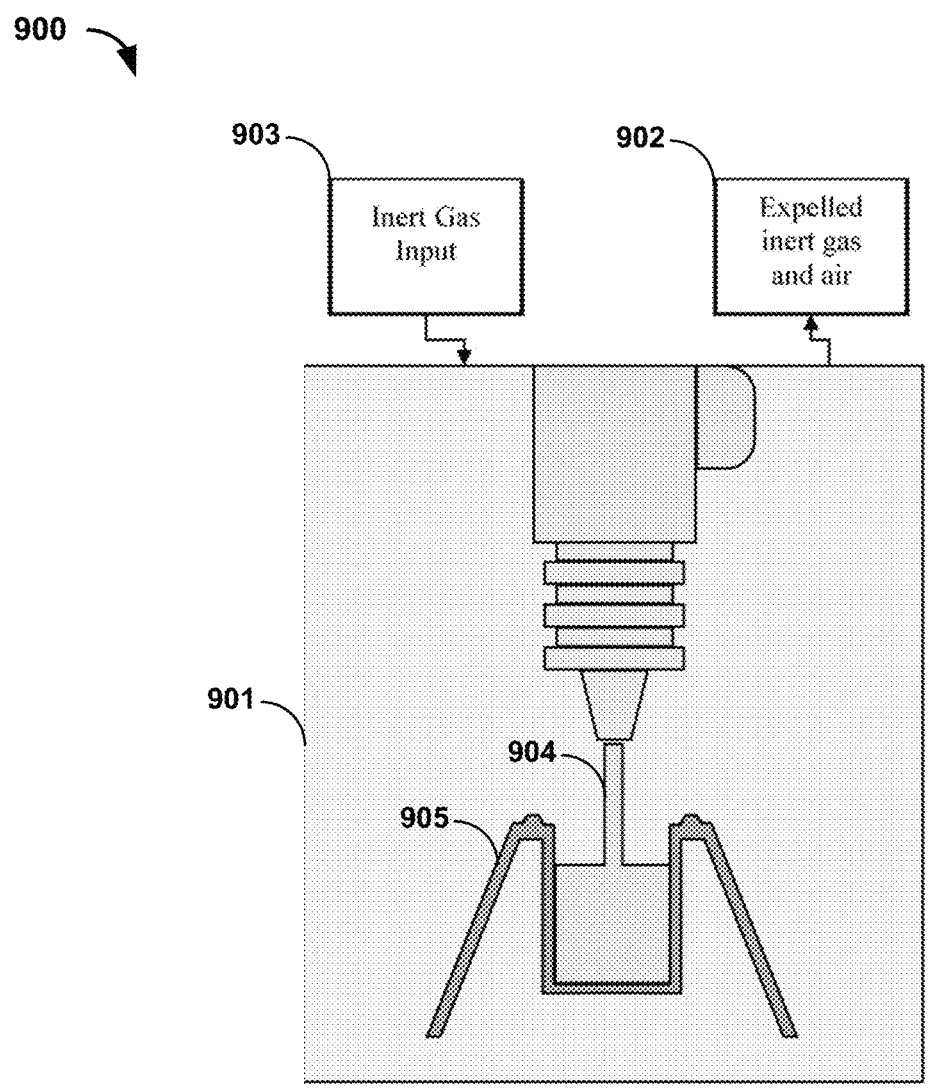
FIG. 9 shows a schematic diagram depicting an example embodiment of a system for dispensing a gel solution to form a SACM in accordance with the present technology.
Figure 10:
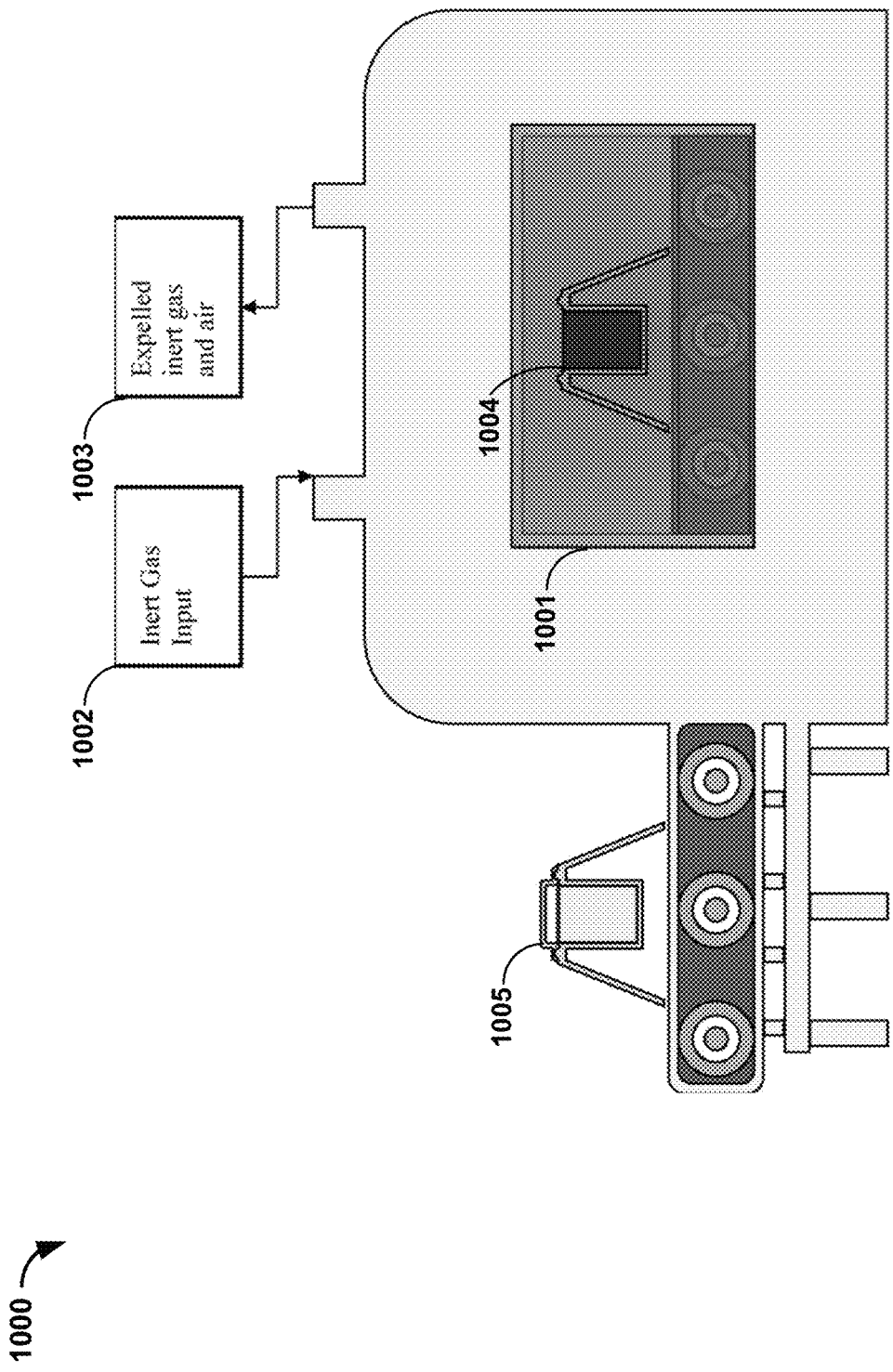
FIG. 10 shows a schematic diagram depicting an example embodiment of a system for gelling, setting, and plotting a gel solution to form a SACM in accordance with the present technology.
Figure 11:
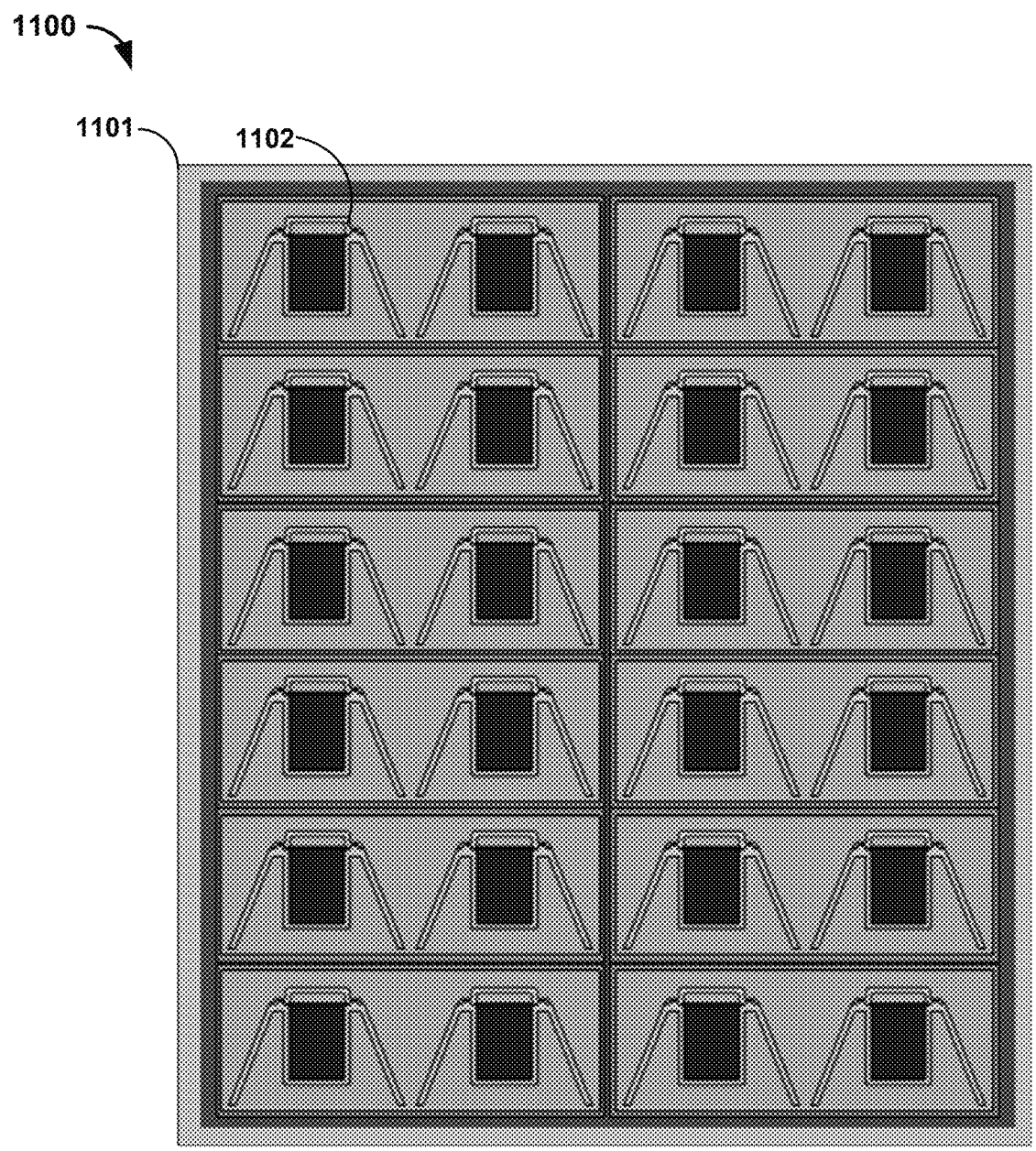
FIG. 11 shows a schematic diagram depicting an example embodiment of a system feature for post-curing SACMs in accordance with the present technology.

FIGS. 9-11 depict schematics of exemplary system features depicting example processes of curing the gel-sol to form the SACMs in accordance with the present technology.

FIG. 9 shows a schematic of an exemplary system 900 for dispensing DAV method of gel-sol accordance with the present technology. In a first step, residual inert gas and air 902 is expelled from the enclosed hood/chamber 901 with inert gas 903. Using the DAV method, the gel-sol 904 is dispensed without incorporating bubbles into the PETG trays 905 under an inert atmosphere. The potted gel-sol in the PETG trays is then cured and/or sets in an oven.

FIG. 10 shows a schematic of an exemplary system 1000 for gelling, setting, and/or potting the gel-sol 1004 in an oven in accordance with the present technology. An oven 1001 such as a laminar flow UV cure oven is flushed out to remove air with inert gas. To expel residual inert gas and air 1003 from the oven, inert gas 1002 flows through the oven 1001 to blanket at the gel-sol 1004 under an inert atmosphere. The gel-sol 1004 is then allowed to gel, set, and/or pot via redox reactions alone or potting can be accelerated with the addition of irradiation (e.g., UV, gamma, or ion-bean irradiation) in the oven 1001. While under an inert atmosphere, the resulting gel (e.g., after gel, set, and/or pot) is sealed with a lid (e.g., a foil lid) and PETG retainer lid to prevent oxygen during transportation. Once set, the sealed gel 1005 is removed from the oven. The sealed gel 1005 when removed from the oven 1001 is a "green" SACM.

FIG. 11 shows a schematic of an exemplary system module 1100 for post curing and dwell time of the gel in accordance with the present technology. For example, the sealed gel 1102, the sealed gel 1004 as referred to in FIG. 10, is placed inside a UV chamber 1101 to accelerate the curing process, reduce residual monomer, and sterilize the product. This step allows the gel to completely cure via redox initiator initiated free radical addition polymerization in an isothermal temperature chamber. The sealed gel 1102 is then irradiated (e.g., with UV, gamma, or ion-bean irradiation) to reduce residual monomer and sterilize the resulting SACMs while still green (e.g., dwell time (e.g., 8 hr)).

Figure 12:
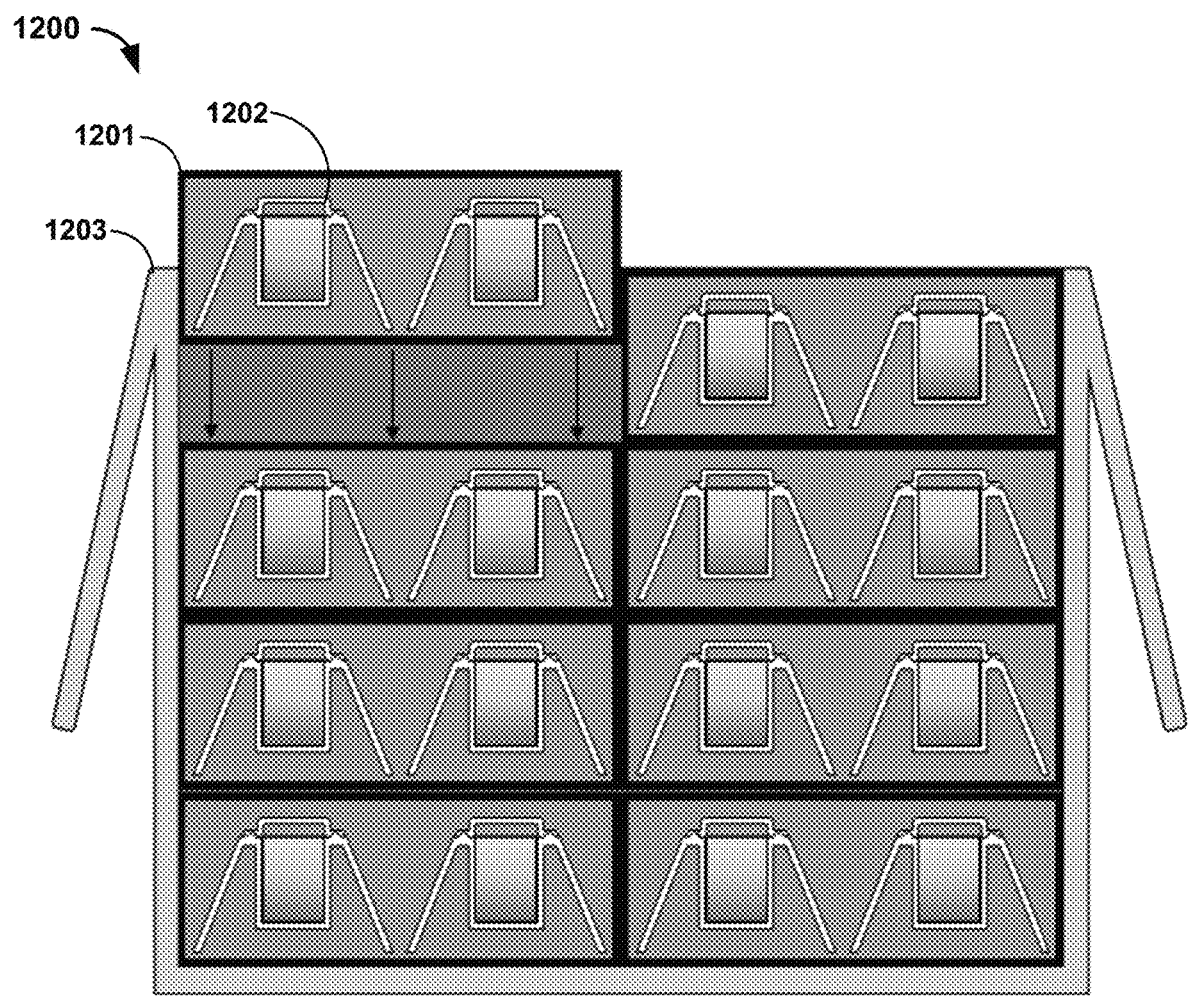
FIG. 12 shows a schematic diagram depicting an example embodiment of a system feature for packing of SACMs in cartons for shipment in accordance with the present technology.

FIG. 12 shows a schematic of an exemplary system module 1200 for packing the SACMs 1202 for transport. For example, after the SACMs 1202 have fully cured and quality assurance tests have been conducted to check for residual monomer, bubbles, detritus, acoustic properties and mechanical properties. The SACMs 1202 are then packed as shown in FIG. 12 and placed in dark, dry cartons 1201, which are then loaded into a box 1203 for shipment.

Figure 13:
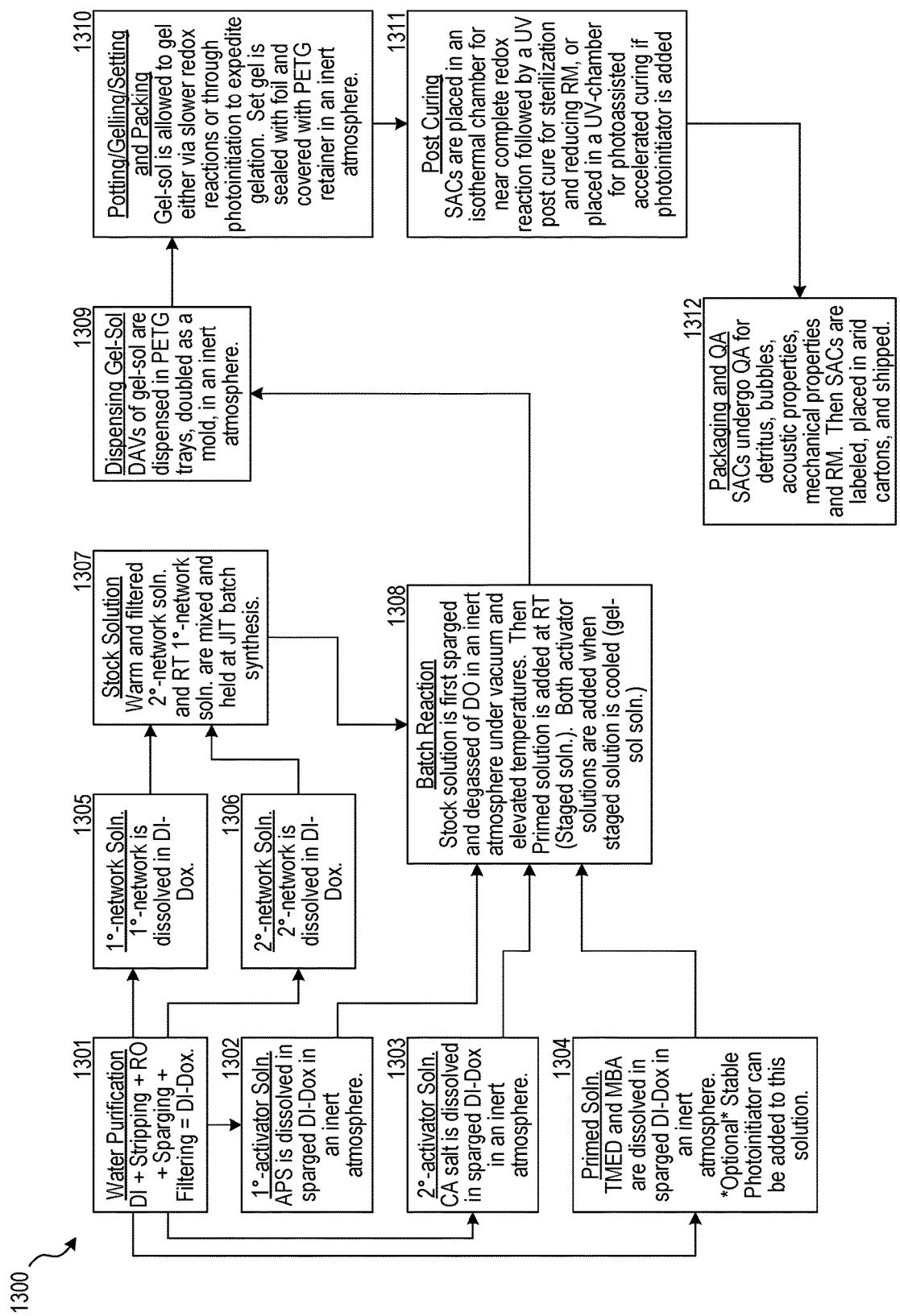
FIG. 13 shows a flow chart of an example embodiment of a method for fabricating a SACM in accordance with the present technology.

FIG. 13 shows a flow diagram depicting an example method, labeled 1300, for producing SACMs in accordance with the example embodiments of the method 300 and 500. In the example shown in FIG. 13, the method 1300 includes a preprocess water purification phase 1301 in which deionized water is stripped, sparged, reverse osmosis (RO), and filtered to produce a DI-DOX solution. The DI-DOX solution is then divided into five separate vessels and to each vessel is added each of the components necessary to form the exemplary SACM. Specifically, the method 1300 includes a process 1302 comprising dissolving APS in DI-DOX in a first vessel under an inert atmosphere to form a 1° activator solution; a process 1303 comprising dissolving CA in DI-DOX in a second vessel under an inert atmosphere to form a 2° activator solution 1303; a process 1304 comprising dissolving a 1° network crosslinking agent (e.g., MBA) and a catalyst (e.g., TMED) to a third vessel of the DI-DOX solution to from a primed solution, which optionally can include adding a photoinitiator; a process 1305 comprising dissolving the 1° network component (e.g., DMA) in a fourth vessel of the DI-DOX solution to form the 1° network solution; and a process 1306 comprising dissolving the 2° network component (e.g., SA) in a fifth vessel to form a the 2° network solution 1306. The method 1300 includes a process 1307 to produce the stock solution including adding the 1° network solution maintained at room temperature (e.g., 23° C.) to the 2° network solution which has been previously warmed and filtered to remove unwanted side product (e.g., fisheye aggregates), the resulting stock solution is then held at STP for subsequent, small batches of gel-sol. In some implementations of the method 1300, for example, the process 1307 includes using the stock solution produced by the method 300. The method 1300 further includes a process 1308 including sparging and degassing the stock solution of DO in an inert atmosphere under vacuum and at elevated temperatures and next, adding the primed solution to the stock solution at room temperature (e.g., 23° C.) to form the staged solution. The staged solution is then cooled (e.g., 15° C.) and then the both 1° activator solution and 2° activator solution are added to the staged solution simultaneously to form a gel-sol (e.g., the batch reaction). The method includes a process 1309 to dispense the gel-sol by pouring DAVs of gel-sol into a mold (e.g., PETG trays) in an inert atmosphere to produce a molded gel-sol in a shape, size, and/or geometry desired for a semi-rigid acoustic couplant. In some implementations of the method 1300, for example, the process 1309 includes using the gel-sol produced by method 500. The method can further include a process 1310 to pot, gel, set, and then package the molded gel-sol including allowing the molded gel-sol to gel and/or pot by first slowing redox initiation, then increasing the rate of reaction through photoinitiation thereby expediting gelation. Once the gel-sol is set the SACM is formed and then sealed (e.g., with foil) and covered with a PETG retainer in an inert atmosphere. The method includes a process 1311 to cure the SACM including placing the SACM in an isothermal chamber to provide completion and/or near completion of the redox reactions followed by irradiation with light (e.g., UV) to post cure the SACM. The post curing process sterilizes and reduces residual monomer. Optionally, if a photoinitiator was added in process 1304, the SACM can be placed in a UV-chamber to accelerate photocuring. Lastly, the method 1300 includes a process 1312 in which the SACMs undergo a quality assurance (QA) test to check for detritus, bubbles, acoustic properties, mechanical properties, and residual monomer. The SACMs are then labeled, placed in arid cartons, and shipped to desired locations. In some implementations of the methods 300, 500 and/or 1300, the manufacturing follows U.S. Food and Drug Administration (FDA) Good Manufacturing Practices (GMP) to reduce the amount of external contamination from air and processing equipment.

Figure 14:
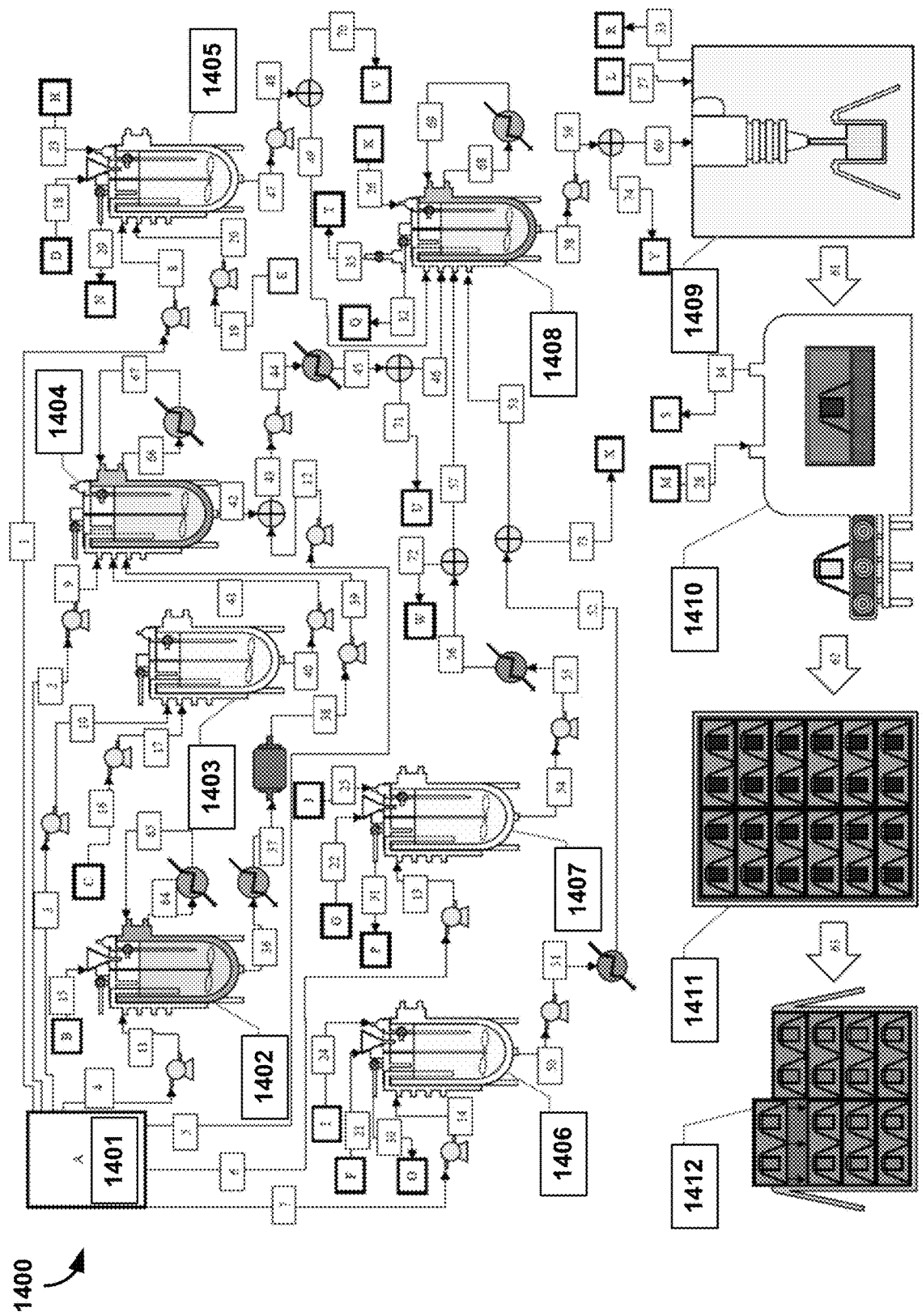
FIG. 14 shows a flow diagram depicting an exemplary process for manufacturing SACMs using an example system and processing steps described in FIGS. 8-12 in accordance with the present technology.

FIG. 14 is a flow diagram depicting an exemplary process 1400 for manufacturing SACMs using an example system and processing steps described in FIGS. 8-12. In system 1401, water is purified, deionized, and deoxygenated via sparging and under reduced pressure (e.g., under vacuum) to produce and/or procure Di-Dox water. The Di-Dox water can then be transferred to each of the downstream operations and/or steps of the exemplary process 1400 as described below.

In some embodiments, the Di-dox water is pumped into the system 1402, which includes a shear mixer vessel for agitating the water before SA is added. The Di-Dox water is heated to a temperature of 60° C. or more in system 1402. Agglomerated, crystalline or powdered SA is then added to the Di-Dox water in the system 1402. The Di-Dox water and the SA are then mixed in the system 1402 to form the 2° network solution. The 2° network solution is then pumped out of the system 1402 through an inline filter or other fisheye separator into the system 1404 to prepare the stock solution.

In some embodiments, the Di-DOX water is pumped into the system 1403 from the system 1401. Crystalline, powdered, agglomerated, or liquid DMA monomer is then added to the Di-Dox water in system 1403. The Di-Dox water and DMA are then mixed until the DMA is fully dispersed and solvated in the Di-Dox water to form the 1° network solution. The 1° network solution is then heated until it reaches room temperature (e.g., 25° C.) and then 1° network solution is then pumped into the system 1404.

The warm 2° network solution (e.g., >37° C.) and 1° network solution from the systems 1402 and 1403, respectively are then mixed until homogeneous in the system 1404 to produce the stock solution. The stock solution is gently stirred and maintained at room temperature for the subsequent processing steps. Each time new batch of the gel-sol is prepared, the stock solution is heated to reduce the solution viscosity (e.g., >37° C.) and then pumped to the system 1408.

In some embodiments, the Di-Dox water is pumped into the system 1405 from the system 1401 and sparged with inert gas under an inert atmosphere. TMED is then pumped and/or poured into the Di-Dox water under constant agitation (e.g., stirring and/or mixing). Agglomerated, crystalline, or powder MBA is then added to the TMED and Di-Dox solution. The TMED and MBA are then mixed until fully dissolved, resulting in the primed-solution. While mixing, the primed solution is sparged with inert gas under and inert atmosphere. The primed solution is then pumped to the system 1408 to form the staged solution. Optionally, the 1° network photoinitiator can be added to the staged solution to supplant and/or to be used with the 1° network redox-initiator.

In some embodiments, the Di-Dox water is pumped into the system 1406 and sparged with inert gas under an inert atmosphere from the system 1401. Agglomerated, powder, or crystalline APS is then added to the Di-Dox water in the system 1406. Under and inert atmosphere the APS is dissolved to make the 1° activator solution. The 1° activator solution is then chilled (e.g., <15° C.) before being pumped into the system 1408 to produce the gel-sol solution.

In some embodiments, the Di-Dox water is pumped into the system 1407 and sparged with inert gas under an inert atmosphere from the system 1401. CA is then added to the Di-Dox water in the system 1407. Under and inert atmosphere the CA is dissolved to make the 2° activator solution. The 2° activator solution is then chilled, heated, or maintained at room temperature before being pumped into the system 1408 to make the gel-sol solution.

Each of the solutions prepared in systems 1404, 1405, 1406, and 1407 are pumped into the system 1408 to form the gel-sol solution. As enumerated above, the warmed stock solution (e.g., >37° C.) is pumped into the system 1408 from the system 1404 and then sparged with inert gas under vacuum while heated (e.g., >50° C.) to remove exogenous oxygen. Next, the solution is cooled in the system 1408, while the primed solution is pumped into the system 1408 from the system 1405 to from the staged solution under an inert atmosphere. The staged solution is then cooled (e.g., >20° C.) while being continuously stirred. The 1° activator solution (e.g., >15° C.) is then pumped into the system 1408 from the system from the system 1407. The 1° activator solution and 2° activator solution are then homogenously dispersed throughout the staged solution in the system 1408 to produce the crosslinked gel-sol solution.

A PETG tray with a desired geometry is then placed in a chamber of system 1409 with a dispensing mechanism. The chamber is then flushed with inert gas to remove oxygen.

The gel-sol is then dispensed into PETG trays via DAV dispensing. The PETG trays are then moved from the system 1409 and into the curing oven of system 1410. The oven of system 1410 is continuously flushed with inert gas. The temperature of the oven is then increased to crosslink the dispensed gel-sol from the system 1409. The gel-sol in the oven can be optionally irradiated with UV-light, ☐-radiation, or EBI to expedite curing and/or to replace the redox reaction step. The hydrogel matrix is then formed via accelerated crosslinking but is not fully cured (i.e., the hydrogel is still "green"). Next, a foil barrier and PETG lids are placed over the hydrogel matrix to seal the trays and to prevent adventitious materials and/or microbes from contaminating the hydrogel matrix.

The hydrogel matrix is then transferred to system 1411 where it is post cured in a UV-chamber to react any residual DMA monomer and to sterilize the hydrogel. After post curing, the hydrogel is fully cured, forming the SACM. Next, the SACMs are inspected for detritus and/or bubbles as well as tested for residual monomer, acoustic properties, and/or mechanical characteristics. The SACMs are then packed in system 1412 and shipped to a vendor and/or customer.

Table 3A shows a legend for an example embodiment of the process unit-operations shown in the diagram of FIG. 14.

TABLE 3A

| Unit-Op(s) | Description |
|---|---|
| 1401 | Water is purified and deionized to make ASTM Type I, II, or III Di-water. Di water is deoxygenated via sparging under vacuum to make Di-Dox. Di-Dox is pumped from system 1401 to each unit operation downstream as needed. |

TABLE 3A-continued

| Unit-Op(s) | Description |
|---|---|
| 1402 | Di-Dox is pumped into the shear mixer vessel of system 1402 and the temperature is increased above 60° C.<br>The shear mixer starts agitating the water before SA is added.<br>Agglomerated, crystalline, or powdered SA is then added into the water.<br>The solution is mixed until the SA is fully solvated to make the 2° network solution.<br>Dissolved, hot 2° network solution (>50° C.) is pumped from the mixer, through an inline filter or other fisheye separator, into system 1404 to make the stock solution. |
| 1403 | Di-Dox is pumped into a system 1403.<br>Crystalline, powdered, agglomerated, or liquid DMA monomer is added to the Di-Dox water.<br>Solution is agitated until DMA is fully dispersed and solvated in the Di-Dox water to make the 1°-solution.<br>1° network solution is heated until it reaches room temperature.<br>1° network solution is pumped to system 1404 to make the stock solution. |
| 1404 | Warm 2° network solution (>37° C.) and room temperature 1° network solution are pumped from systems 1402 and 1403, respectively into the system 1404 and mixed until homogenous to make the stock-solution.<br>The stock solution is gently stirred and kept at room temperature for the subsequent JIT processing steps to manufacture SACMs.<br>For starting a new batch of gel-sol, the stock-solution is heated to reduce the solution viscosity (>37° C.) and then pumped to system 1408. |
| 1405 | Di-Dox is pumped into the system 1405 and sparged with inert gas under an inert atmosphere<br>TMED is pumped or poured into the Di-Dox under constant agitation<br>Agglomerated, crystalline, or powdered MBA is poured into the mixer<br>TMED and MBA are mixed until dissolved to form the primed-solution.<br>While mixing the primed-solution is sparged with inert gas under an inert atmosphere<br>Optionally, a 1° network photoinitiator can be added while mixing the staged solution to supplant or be used with the 1° network redox-initiator<br>Primed-solution is pumped to system 1408 to make the staged-solution. |
| 1406 | Di-Dox is pumped into the system 1406 and sparged with inert gas under an inert atmosphere.<br>Agglomerated, powdered, or crystalline APS is poured into the system 1406.<br>Under an inert atmosphere the APS is quickly dissolved to make the 1°-activator solution.<br>1°-activator solution is chilled (<15° C.) before pumped into system 1408 to make the gel-sol solution. |
| 1407 | Di-Dox is pumped into the system 1407 and sparged with inert gas under an inert atmosphere.<br>CA is poured into the system 1407.<br>Under an inert atmosphere the CA is quickly dissolved to make the 2°-activator solution.<br>2°-activator solution is chilled, heated, or remains at room temperature before pumped into system 1408 to make the gel-sol solution. |
| 1408 | Warm stock solution (>37° C.) is pumped from system 1404 into the system 1408 and then sparged with inert gas under vacuum while heated (>50° C.) to remove exogenous oxygen.<br>Stock-solution is cooled while primed-solution is pumped from system 1405 into the stock solution to form the staged-solution under an inert atmosphere.<br>Staged solution is chilled (<20° C.) while continuously stirring.<br>The chilled 1°-activator solution (<15° C.) is pumped from system 1406 and mixed into the staged solution.<br>Depending on the temperature of the admixture, either chilled, room-temperature, or heated 2°-activator solution is pumped from system 1407 and mixed into the staged solution.<br>Under constant agitation, the 1°-activator and 2°-activator solutions are homogenously dispersed throughout the staged-solution, forming the now crosslinking gel-sol.<br>Gel-sol is pumped to the dispenser system 1409 to pour-cast DAVs of gel-sol into the plastic trays. |
| 1409 | A PETG tray with the desired geometry is placed in the chamber of system 1409 with the dispenser.<br>The chamber is flushed with inert gas to remove oxygen<br>A DAV of gel-sol is dispensed into the tray from the dispenser<br>The tray then moves from the dispenser to the curing oven of system 1410 |

TABLE 3A-continued

| Unit-Op(s) | Description |
|---|---|
| 1410 | The oven of system 1410 is continuously flushed with a blanket of inert gas |
|  | The oven temperature is increased to crosslink the dispensed gel-sol from 1409 |
|  | Optionally the gel-sol can be irradiated to with UV-light, γ-radiation, or EBI to expedite curing or replace the redox reaction step |
|  | The hydrogel matrix is formed via accelerated crosslinking reactions but is not fully cured - i.e. the hydrogel is still green. |
|  | A foil barrier and PETG lid seals the green hydrogel against adventitious material and microbes |
| 1411 | Green hydrogel is post cured in a UV-chamber of system 1411 to react residual DMA monomer and to sterilize hydrogel. |
|  | Hydrogel is fully cured, forming the SACM |
| 1412 | SACMs are inspected for detritus and bubbles. |
|  | SACMs are tested for residual monomer, acoustic properties, and mechanical characteristics. |
|  | SACMs are packaged in system 1412 and shipped to vendor/customer. |

Table 3B shows the legend for the process streams shown in the diagram of FIG. 14.

TABLE 3B

| Stream(s) | Description |
|---|---|
| 1-14 | DI-Dox water streams from system 1401 under pressure head for mixing and flushing procedures. |
| 15 | SA pellets are poured into system 1402 containing DI-Dox water for swelling and solvation. |
| 16-17 | Liquid DMAm monomer is fed into system 1403 containing DI-Dox. |
| 18 | Powdered MBA is poured into the system 1405 mixer to be dissolved with sparged DI-Dox and TMED to form the primed solution. |
| 19-20 | Liquid TMED is fed into the system 1405 mixer to be solvated with MBA and sparged DI-Dox to form the primed solution. |
| 21 | Crystalline APS is dissolved in sparged DI-Dox in system 1406 to form the 1°-activator solution. |
| 22 | CA salts are dissolved in sparged DI-Dox in system 1407 to form the 2°-activator solution. |
| 23-28 | Pressurized, inert gas feed streams for sparging and/or inert atmosphere blanket. |
| 29-34 | Gaseous purge stream to remove evacuated oxygen and inert gas from solutions and vessel overhead. |
| 35 | Applied vacuum with water trap to reduce overhead pressure for easier inert gas and oxygen bubble removal during system 1408 sparging. |
| 36-37 | Warm, viscous, and concentrated SA solution is heated prior to fisheye filtration to reduce the solution viscosity, but not too warm for polysaccharide degradation. |
| 37-38 | Hot, less viscous, and concentrated SA solution passes through a filter to remove fisheyes before passing through the pump and going into system 1404. |
| 38-39 | Warm, filtered SA solution is pumped into system 1404 with DMAm solution to make the stock solution. SA solution heated depending on SA solution viscosity. |
| 40-41 | DMAm solution from 1403 is pumped into system 1404 to make the stock solution. |
| 42-46 | Warmed stock solution feed stream into batch reactor system 1408. Warmed to lower viscosity and prep the stock solution for degassing and sparging. |
| 12, 43-46 | Flush stream to push residual stock solution in pipes into the batch reactor to prevent pipe fouling and caking by pumping DI-Dox from system 1401. Also doubles as a DI-Dox feed stream to makeup the water lost from vaporized water leaving solution. |
| 42-45, 71 | system 1404 CLIP flush stream. |
| 47-49 | Primed Solution feed stream into batch reactor system 1408 to make staged solution. |
| 47-48, 70 | system 1405 CLIP flush stream. |
| 50-53 | Chilled 1°-activator solution pumped into batch reactor system 1408 to begin vinyl addition polymerization. Chilled to lower rate of reaction. |
| 50-52, 73 | system 1406 CLIP flush stream. |
| 54-57 | Room temperature, heated, or chilled 2°-activator solution fed into system 1408 batch reactor. Cooled of additional temperature decrease is needed. |
| 54-56, 72 | system 1407 CLIP flush stream. |
| 58-60 | Gel-sol DAV stream for dispensing gel-sol in plastic tray packaging that doubles as a mold. |
| 58-59, 74 | system 1408 CLIP flush stream. |

TABLE 3B-continued

| Stream(s) | Description |
|---|---|
| 61 | Dispensed gel-sol is allowed to pot via redox reaction or is accelerated vi UV exposure. Potted solution is sealed with foil cover and retainer lid. |
| 62 | Potted solution is post UV cured to reduce residual monomer and sterilize SACs. Also, extra UV curing decreases the cure dwell time. |
| 63 | Fully cured SACs are packaged for shipment in dark, arid cartons. |
| 64-65 | Water in system 1402 water jacket is heated to warm SA solution prior to pumping to lower the viscosity. |
| 66-67 | Water in system 1404 water jacket is either heated or cooled to maintain near constant room temperature stock solution. |
| 44-45 | Stock solution heated more efficiently via counter-convective heat exchange than stock solution agitation and heating for system 1404. Stock solution is heated for inert gas and oxygen removal under vacuum and inert gas sparging. |
| 68-69 | Solution is first kept warm to lower viscosity during sparging and degassing protocols. Then solution is cooled before reaction is initiated to prevent rapid, auto-accelerated reactions. During vinyl addition reactions, the temperature is also controlled to be around room temperature. |
| 50-51 | 1°-activator solution is chilled to reduce rate of reaction. |
| 50-52 | 2°-activator solution is chilled to if vinyl addition rate of polymerization needs to be reduced further. |

Example Implementations of SACMs

The example embodiments described above can be used to produce a variety of semi-rigid acoustic couplant materials, such as hydrogel interface pads (HIP), in some implementations. Examples implementations of SACMs are described below.

The mesh size of a hydrogel is dependent on various parameters to include the reaction rate, chain length, stereochemistry, intramolecular interactions, and reaction conditions such as temperature, pressure, and the atmosphere.

In some implementations of the method 300, 500, and 800, for example, an important consideration in making a SACM involves a judicious choice in the quantity of the both the cationic crosslinking agent and the covalent crosslinking agent. For example, in the present exemplary method of making the SACM, the addition of too much of CA (i.e., cationic crosslinking agent) results in the formation of super-aggregates whereas too little CA results in the formation super-dispersions. The equilibrium of too little CA (e.g., super-dispersions) and too much CA (i.e., super-aggregates). Similarly, too much MBAm (i.e., covalent crosslinking agent) results in a tiny mesh size whereas too little MBAm results in too large of a mesh size. As such, the methods 300, 500 and/or 1300 may use 0.14-0.23 wt % of CA and 8.29-9.8 wt % of MBAm in the fabrication of some embodiments of the SACM provided an optimal degree of aggregation and mesh size.

An additional consideration, crucial to fabricating pliable and robust SACMs, is the degree of grafting that occurs upon reacting the secondary, grafted sacrificial network component (e.g., sodium alginate) and the primary, structural network component (e.g., DMAm). Grafting provides impact strength, energy dissipation, self-healing properties, mechanical hysteresis, and thermal hysteresis of the SACM. The exemplary SACM of the present disclosure exhibits and optimal degree of grafting between the SA and DMAm that affords the aforementioned characteristics.

Figure 15:
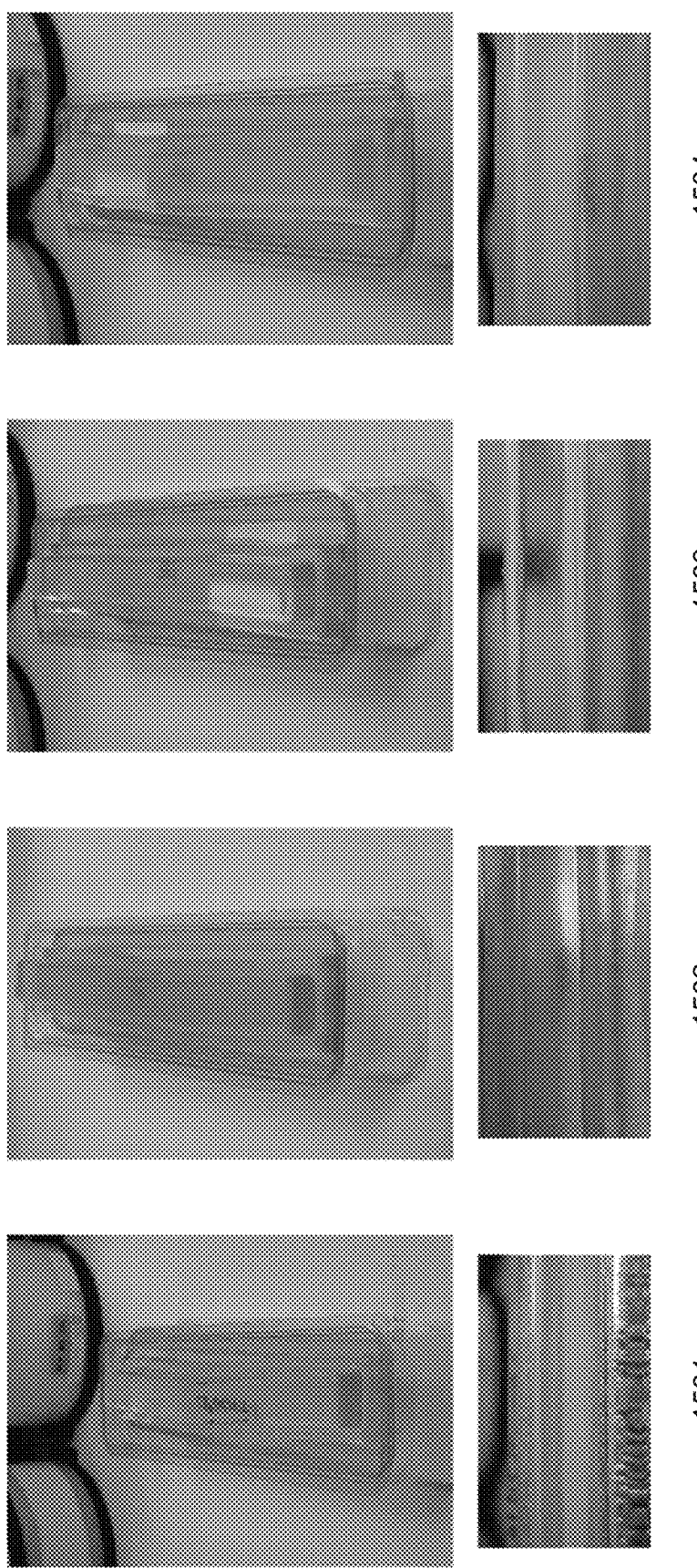
FIG. 15 shows images of example acoustic couplants including an example SACM in accordance with the present technology used in example implementations for evaluating acoustic and mechanical properties of the couplants.

FIG. 15 shows pictures of sample hydrogel interface pads 1502, 1503, 1504 fabricated using the disclosed techniques but with varying amounts of constituents, and of a hydrogel interface pad 1501 fabricated using a conventional composition with conventional techniques.

In example implementations, the example SACM 1501 was used as a control hydrogel, composed of Poly(Acrylamide) (Poly(AA)) with low viscosity P(SA) 2° network with good elastic, conformability, and clarity properties.

Rippling on SACM 1501 exposed surface was due to surface tension differentials during the gelation process. The example SACM 1503 was configured to have the same composition as SACM 1501 without surface rippling. The example SACM 1504 was configured to have the same composition of Poly(AA) and P(SA) components as SACM 1501 and SACM 1503; but, the example SACM 1504 supplements low viscosity P(SA) with high viscosity P(SA). The example SACM 1502 was configured to have the same composition of P(SA) as SACM 1501 and SACM 1503 while substituting Poly(DMAm) for Poly(AA). In these implementations, it was shown that all of the example SACMs had similar acoustic properties while only differentiating in elastic modulus (E) and Ultimate tensile strength (UTS).

Figure 16:
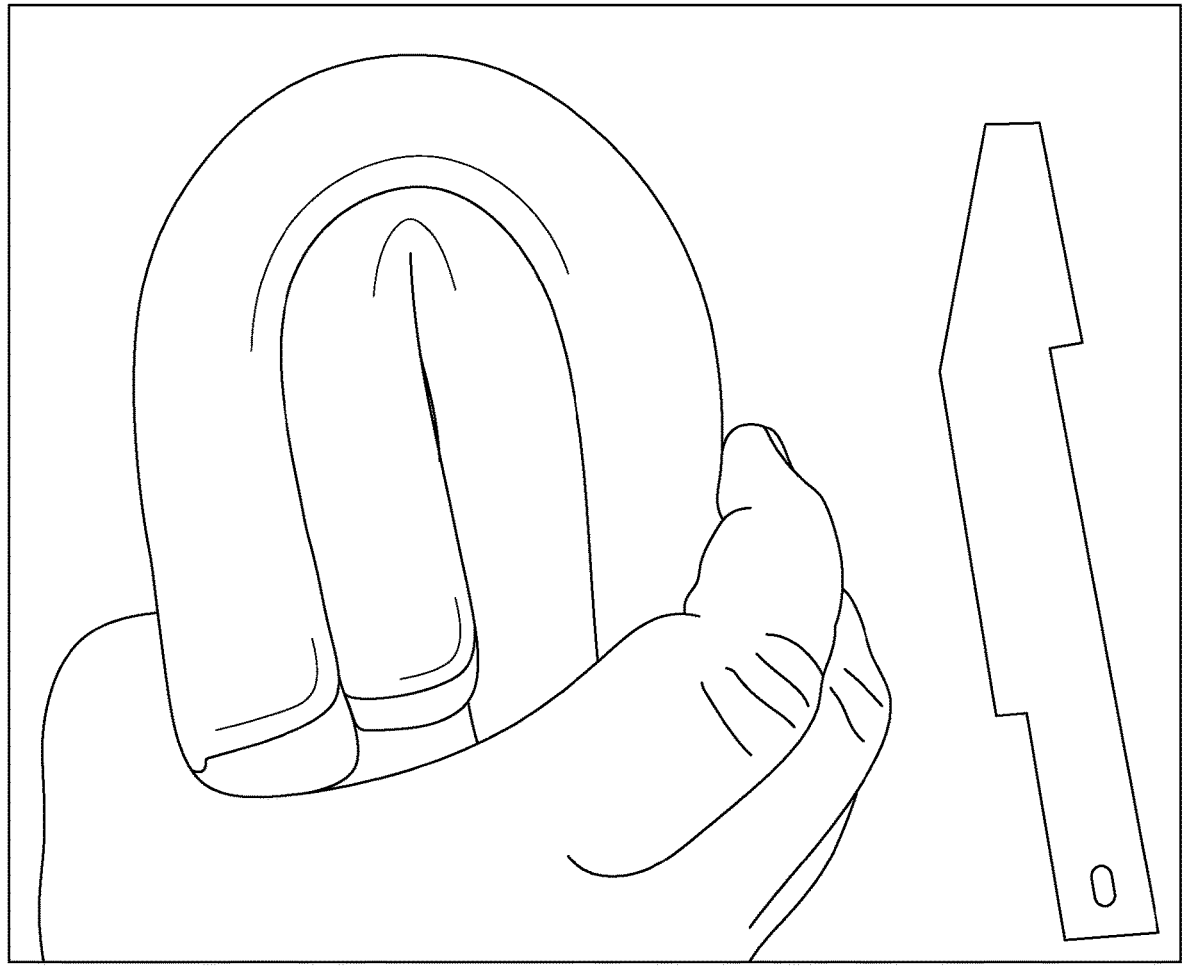
FIG. 16 shows an image of an example ionically, cross-linked hydrogel interface pad.

For example, rippling on the transducer side of SACM 1501 was due to interfacial tension between the air and solution boundary during gelation, causing the gel surface to buckle and warp. SACM 1503 reduced the interfacial surface tension during gelation, negating all rippling. SACM 1504 supplemented low viscosity P(SA) with high viscosity P(SA) which reduced the elastic modulus considerably, yielding a softer, more pliable SACM. In these example implementations, the most pliable was the SACM 1502 which had the lowest elastic modulus while exhibiting similar toughness and acoustic energy transmission properties. By further tuning SACM 1502 crosslinking rate of reaction, processing variables, and the concentration and types of constituents, a variety of different mechanical properties can be achieved for a plethora of US examination applications without sacrificing good acoustic transmission. As an extreme example, a variant of SAM 1502 (SACM 1502') had the same SOS, ATTN, and Z as SACM 1502 was overly crosslinked to yield a flexible, stiff hydrogel as shown in FIG. 16. Adding excessive divalent ion crosslinker did not affect the SOS (e.g., 1549 m/s), ATTN (e.g., 0.07 dB/cm*MHz), and clarity while exhibiting an elastic modulus (e.g., 302 kPa) drastically different from SACM 1502.

FIG. 16 shows an image of an example ionically, cross-linked hydrogel interface pad.

Table 4 show tested acoustic and mechanical properties of the SACM samples 1502, 1503, and 1504 and for an example control hydrogel sample 1501. Note, in Table 4, "SOS" stands for speed of sound; "Z" is acoustic impedance, "ATTN" is attenuation, "E" is the Young's Modulus, and "ε" is the engineering strain.

TABLE 4

| Hydrogel Sample (#) | SOS (m/s) | Z (MRayls) | ATTN (dB/cm/MHz) | E (kPa) | ε (mm) |
|---|---|---|---|---|---|
| 1501 | 1548 | 1.595 | 0.14 | 48 | −15 |
| 1502 | 1549 | 1.597 | 0.14 | 32 | −15 |
| 1503 | 1547 | 1.594 | 0.08 | 46 | −15 |
| 1504 | 1547 | 1.594 | 0.03 | 40 | −15 |

The composition of the SACM has been tailored to create a soft, compliable hydrogel that can conform and envelop the target site to bridge the air acoustic impedance boundary and be tough for clinical applications, as demonstrated in FIGS. 17A-17F. By adjusting the SACM composition—covalent and ionic crosslinker, amount and type of 1° network monomer and 2° network block copolymer, and rate of reaction—a range of different mechanical properties can be achieved while maintaining a relatively constant Speed of Sound (SOS), acoustic impedance (Z) and Attenuation (ATTN) as shown in Table 4.

Figure 17A:
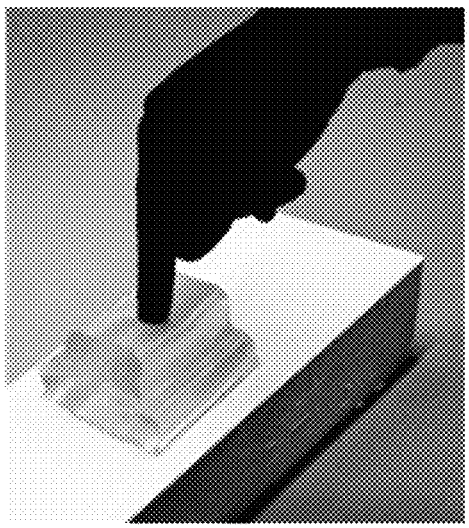
FIGS. 17A-17F show images of an example SACM under mechanical stress.
Figure 17B:
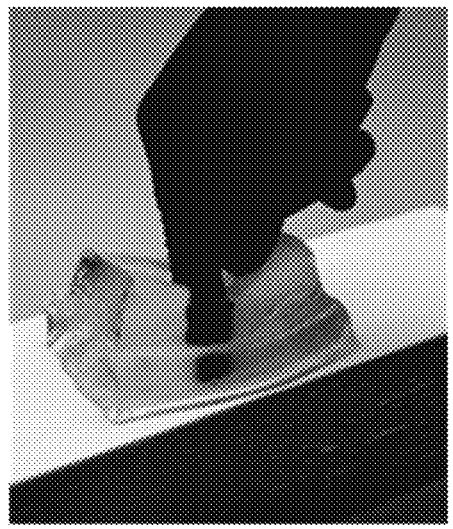
Figure 17C:
Figure 17D:
Figure 17E:
Figure 17F:

FIGS. 17A-17F show images of the pliability, stretchability, and robustness of the example SACM 1502. Specifically, FIG. 17A shows the SACM prior to localized compression, contrasting FIG. 17B which shows the SACM 1502 during localized compression. Similarly, FIG. 17C shows the SACM 1502 prior to squeezing, contrasting FIG. 17D which shows the SACM 1502 during squeezing. Lastly, FIG. 17E shows the SACM 1502 conformability characteristics and FIG. 17F shows the SACM 1502 under full compression. Taken together, these experiments support that the SACM 1502 is resistant to fracturing, which can be attributed to an overall increase in toughness and elasticity.

Example Implementations of the Chemistry Used for Fabricating Some Embodiments of SACMs Mechanical properties are also affected by scaling up the of vinyl addition polymerization reaction. Free radical chain reactions are initiated when an initiator generates a free radical monomer or free radical chain intermediate that subsequently generates another free radical monomer or chain intermediate. This process continues until most of the free radicals react while the remaining free radicals are unable to react due to physical forces limiting their reaction.

Initiation:

$$I \rightarrow \dot{R} + \dot{R} \quad (1)$$

$$M + \dot{R} \rightarrow \dot{M}_1 (\text{fast}) \quad (2)$$

$$v_i = k_i[I] \quad (3)$$

Propagation:

$$M + \dot{M}_1 \rightarrow \dot{M}_2 \quad (4)$$

$$M + \dot{M}_{n-1} \rightarrow \dot{M}_n \quad (5)$$

$$v_p = k_p[M][\dot{M}] \quad (6)$$

$$\bar{v}_p = \left(\frac{d[\dot{M}]}{dt}\right)_{production} = 2fk_i[I] \quad (7)$$

Termination:

$$\dot{M}_n + \dot{M}_m \rightarrow M_{m+n} (\text{mutual termination/recombination}) \quad (8)$$

$$\dot{M}_n + \dot{M}_m \rightarrow M_n + M_m (\text{disproportionation}) \quad (9)$$

$$M + \dot{M}_n \rightarrow \dot{M} + M_n (\text{chain transfer}) \quad (10)$$

$$v_t = k_t[\dot{M}]^2 \quad (11)$$

$$\bar{v}_t = \left(\frac{d[\dot{M}]}{dt}\right)_{depletion} = -2k_t[\dot{M}]^2 \quad (12)$$

The initiation step is the fast step of the reaction where the initiator (I) dissociates and generates free radicals (Ṙ) that further generate free radical monomers or chains (Ṁ). The rate of initiation ($v_i$) is the product of the initiation reaction constant ($k_i$) and the initiator concentration.

During the propagation step, free radical chains react with other chains ($M_n$) or monomer (M) which in turn become radicalized. The steady state rate of propagation ($\bar{v}_p$) is the product of the rate initiation constant, the concentration of initiator, and the fraction of successful free radical chain initiations (f), and terminal chain ends reacting with other chains that, in turn, generate new free radical terminal ends. The fraction of successful free radical chain initiations, also known as the initiator efficiency, is dependent upon the solution temperature, viscosity, and steric inhibition.

Termination can result in one of three ways: mutual termination, disproportionation, and chain transfer. Mutual termination results in longer chain lengths, and is thus the desired termination step. Disproportionation results in the termination of free radicals on both chains and results in shorter chain lengths. Chain transfer results in shorter chain lengths for the free radical donor while the free radical receiver becomes chemically active. By assuming chain transfer and disproportionation are minimal, the steady state rate of termination ($\bar{v}_t$) becomes the product of both free radical terminal ends reacting, the termination reaction constant ($k_t$), and the concentration of free radical chains. Assuming mutual termination is the major termination reaction is a reasonable assumption since many acrylamide and acrylate kinetics exhibit greater mutual termination than disproportionation.

From the initiation, propagations, and termination steps a net, steady state reaction formula is generated.

Net Reaction:

$$[\dot{M}] = \left(\frac{fk_i}{k_t}\right)^{0.5}[I]^{0.5} \quad (13)$$

$$\left(\frac{d[\dot{M}]}{dt}\right)_{net} = 2\left(fk_i[I] - k_t[\dot{M}]^2\right) \quad (14)$$

$$v_p = k_p\left(\frac{fk_i}{k_t}\right)^{0.5}[I]^{0.5}[M] = k_r[I]^{0.5}[M] \quad (15)$$

The net rate of propagation ($v_p$) is the product of the overall propagation reaction constant ($k_r$), the concentration of the initiator, and the concentration of the chains or monomers present in the solution A 1½ order reaction indicates the intermediate propagation step in polymerization before terminating. Free radical lysis is the rate limiting step which dictates how much monomer will be consumed.

Because free radicals react quickly with the monomer which is, in turn, less stable than the free radical initiators, the free radical chains react with one another faster than the initiator reacts with the free radical chains. Eventually the free radical initiator is consumed and the reaction proceeds until the radical ends of the long polymer chains mutually terminate.

From the rate of propagation, the degree of polymerization ($\langle N \rangle$) and kinetic chain length (v) can be calculated.

Degree of Polymerization and Kinetic Chain Length $$v = \frac{k_p[\dot{M}][M]}{2k_i[\dot{M}]^2} = \frac{k_p[M]}{2k_t[\dot{M}]} = k_r'[M][I]^{-0.5} \tag{16}$$

$$k_r' = \left(\frac{1}{2}\right)k_p(fk_ik_t)^{-0.5} \tag{17}$$

$$\langle N \rangle = 2v \tag{18}$$

The kinetic chain length is the ratio of the rate of chain propagation and the rate production of free radicals that undergo polymerization (or, create "active centers"); ergo, increasing the concentration of free radical initiator with respect to the concentration of monomer chains will decreases the kinetic chain length since too much monomer will be initiated for free radical addition, causing growing chains to terminate more frequently as the monomer is rapidly expended. The degree of polymerization for linear chains is directly proportional to the kinetic chain length, yielding a two-fold increase in the degree of polymerization since the major mode of termination is recombination.

Because the 1° network is polymerized via vinyl addition reaction, the composition of constituents will have a significant impact on the hydrogel mechanical and acoustic properties. Too much initiator will yield SACMs with extremely short chains that increase the viscosity of the solution but will not create a semi-solid material. On the other hand, too little initiator reduces the rate of reaction to a crawl and can result in higher concentrations of residual monomer if the free radical vinyl addition reaction is quenched before completion.

In a similar manner, excessive catalyst intensifies the rate of initiation and propagation which results in shorter chains lengths resulting in brittle, inelastic SACMs. In turn, minute amounts of catalyst can increase the reaction duration from hours to days. While longer reaction durations can result in longer chain lengths in theory, the increase in solution viscosity during gelation will terminate and propagate less and increase the likelihood of oxygen quenching vinyl addition reactions, resulting in SACMs with significant concentrations of residual monomer and free radicals and greater variability in mechanical properties.

Inordinate amounts of 1° network monomer give SACMs long chain lengths and strength, but also retain considerable amounts of residual monomer as the reaction proceeds toward gelation because the frequency of monomer collisions that continue the propagation steps during polymerization decrease due to an increase in solution viscosity. On the other extreme, infinitesimal amounts of monomer will lower the rate of propagation and residual monomer concentrations, but generate stiff and brittle SACMs since the kinetic chain lengths will be small because not enough monomer is in solution to create long polymer chains.

When scaling up the vinyl addition reaction other factors must be taken into account during the processing. As the batch volume increases, so does the rate of polymerization and the rate of heat generated. If not controlled, auto-accelerated reactions can occur which will generate a positive feedback loop leading rapid temperature and pressure buildup and a possible explosion. Equations 19-21 are used to calculate the enthalpy of polymerization ($\Delta H_p$) by increasing the monomer ($m_{monomer}$) mass with a specific heat ($S_{monomer}$) at a constant water mass ($m_{water}$) and specific heat ($S_{water}$) while observing the change in temperature ($\Delta T$). Molar enthalpies of polymerization $$\left(\Delta H_p\left(\frac{J}{\text{mol}}\right)\right)$$

can be calculated by taking the ratio of the enthalpy of polymerization and moles of monomer ($n_{monomer}$) which is calculated from the mass of monomer and monomer molecular weight ($MW_{monomer}$).

Enthalpy of Polymerization $$\Delta H_p(J) = [m_{water} * S_{water} + m_{monomer} * S_{monomer}] * \Delta T \tag{19}$$

$$\Delta H_p\left(\frac{J}{\text{mol}}\right) = \frac{\Delta H_p}{n_{monomer}} \tag{20}$$

$$n_{monomer} = \frac{m_{monomer}}{MW_{monomer}} \tag{21}$$

An enormous amount of heat can be generated from the exothermic polymerization of the monomer and the cross-linking reactions. For example, if the reaction conditions—like the reaction rate, temperature, pressure, quantity of reagent, and etc.—are not controlled, then the solution will generate more heat than what heat can be removed, leading to a massive rise in solution temperature. Effects of processing and constituent mass on the final product be further explicated by the Arrhenius equation.

Arrhenius equation:

$$k_r' = A * \exp\left[\frac{-E_a}{RT}\right] \tag{19}$$

$$A = Z * \rho' \tag{20}$$

Arrhenius, equations 22-23, states as the solution temperature increases (T), the kinetic energy of the solution increases (RT)—R is the universal gas constant—relative to the activation energy ($E_a$) which also changes based on how the catalyst promoting properties change with temperature. How steric interactions ($\rho'$) and the frequency of effective collisions (Z) effect the pre-exponential factor (A) determines the frequency of collisions in the correct orientation to initiate a reaction. Controllable solution properties that govern the pre-exponential factor are solution viscosity, density, and temperature. Thus, by increasing the temperature of the solution relative to the constant activation energy, the rate of reaction will increase as the kinetic energy of the monomers increase and intensify the number of reactive collisions in solution, increasing the viscosity and, eventually, lead to gelation.

Figure 18:
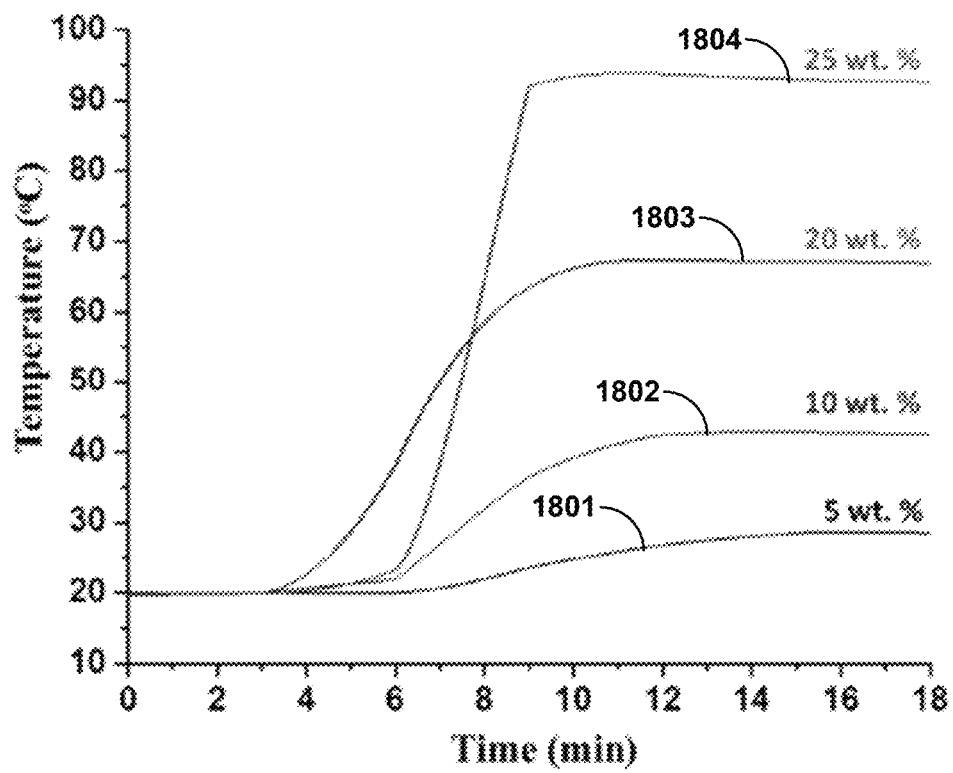
FIG. 18 shows a data plot depicting how the mass of constituents that comprise the SAM affect the reaction rate.

FIG. 18 depicts exemplary plots 1801-1804 illustrating how the mass of the constituents that comprise the SAM affect the reaction rate. For example, the mass of the constituents can affect auto-acceleration, which is demonstrated by the example results of an experiment carried out as shown in exemplary FIG. 18. AAm monomer was increased while keeping the catalyst, initiator, and solvent masses constant. As a consequence, the final solution temperature increased and the rate of rate of temperature increased. Solutions at or exceeding 20 w % AAm rapidly gelled and quickly increased past 60° C.-90° C. with significant amounts of residual monomer and free radicals remaining as shown in Plots 1803 and 1804, which each comprise 20 w % and 25 w % of AAm, respectively. However, the 5 w % AAm solutions barely increased in viscosity as shown by Plot 1801 since there is not enough monomer to form long polymer chains and hardly increased in temperature as a result. In the middle, 10 w % AAm solutions become clear, viscous solutions as the polymer chain length increased and remained in the dispersed phase, not gelling as the reaction progressed as shown by Plot 1802. From this experiment, for example, the importance of controlling the batch size and the vessel surface-area-to-volume-ratio; need to maintain adequate solution temperature, viscosity, and pressure; and, significance of varying the feed rate and concentration of reacting constituents have on the SACM mechanical, acoustic, and biocompatibility properties are evident.

Figure 19A:
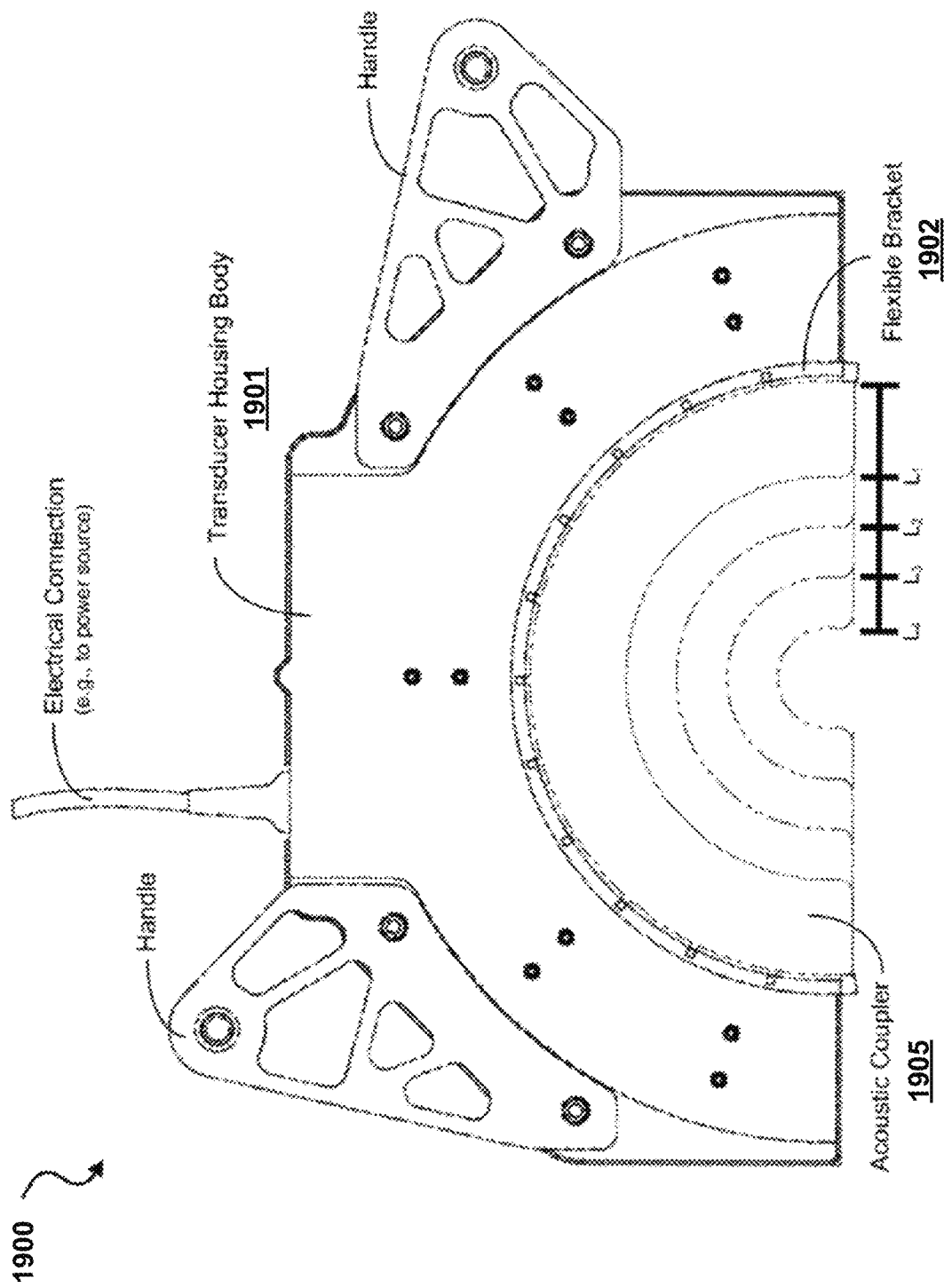
FIGS. 19A-19C shows schematic diagrams of an exemplary acoustic probe device coupled to an example SACM in accordance with the disclosed technology.
Figure 19B:
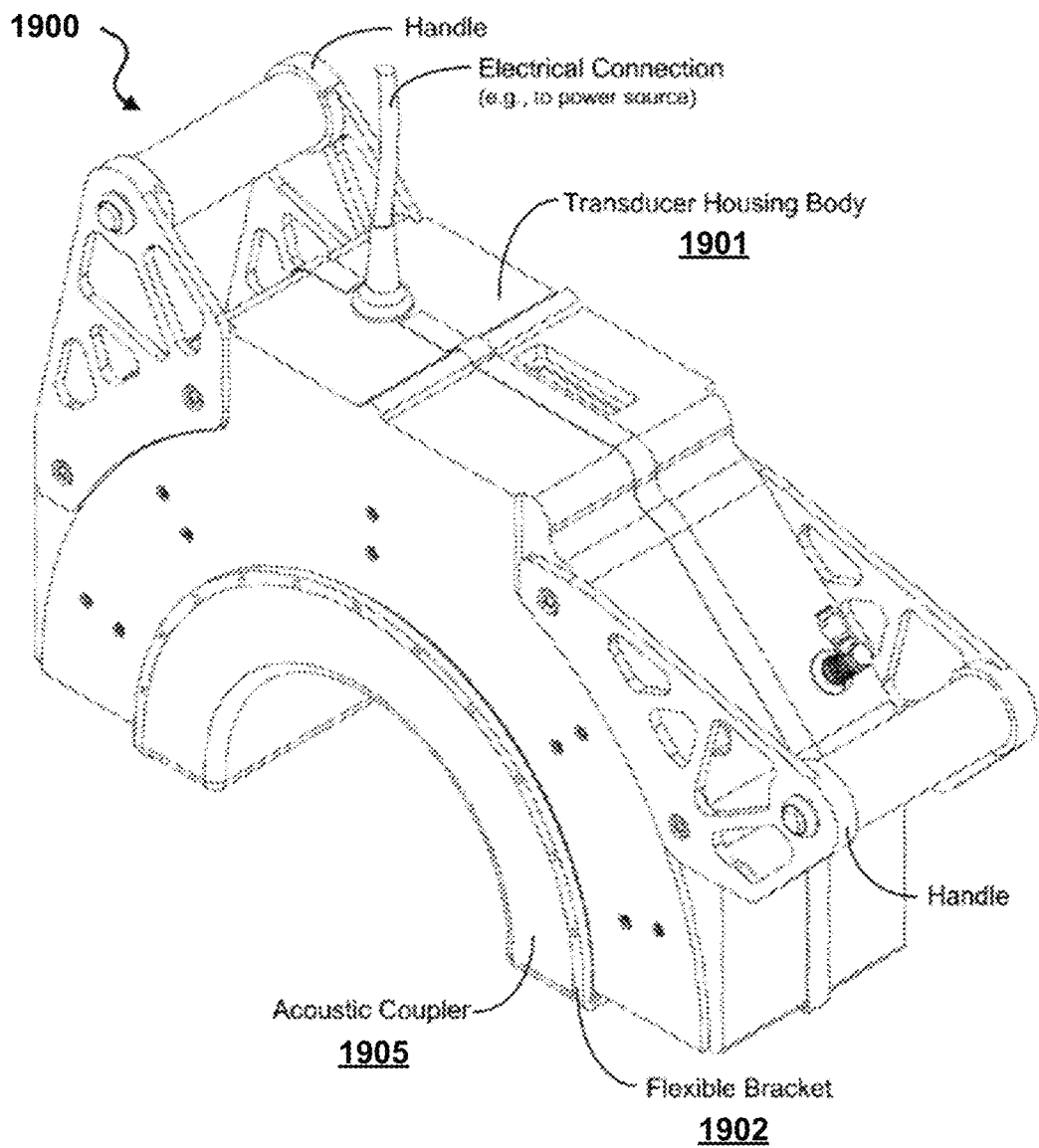
Figure 19C:
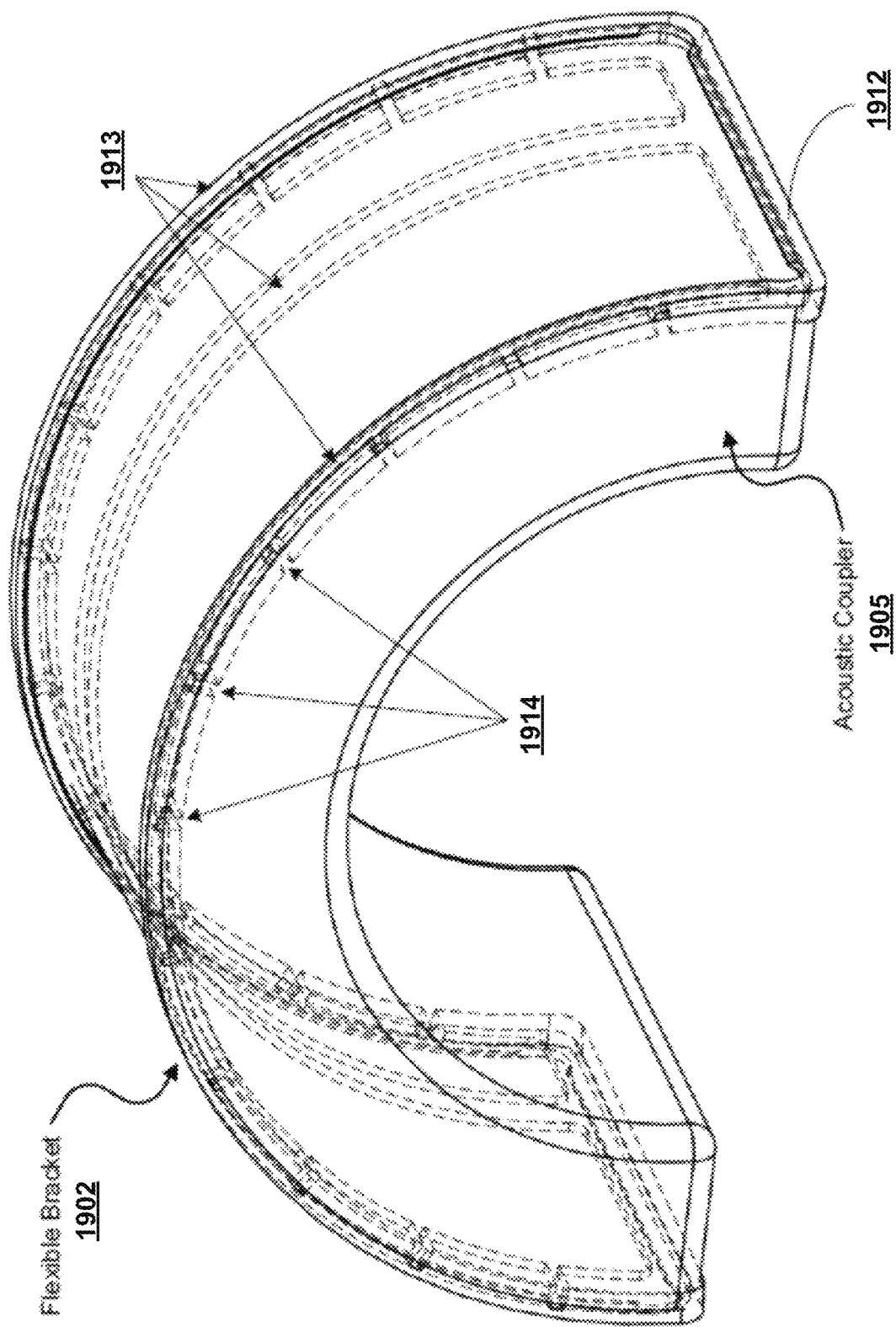

FIGS. 19A-19C show schematic diagrams of an acoustic probe device 1900 in accordance with the example embodiments of the disclosed acoustic couplant medium technology. The probe device 1900 includes a housing structure 1901 to contain and position one or more transducers for transmitting and receiving acoustic signals to/from a mass (e.g., body part) to which the acoustic probe device 1900 is applied. The couplant device 1900 includes an acoustic coupling article 1905 that is an embodiment of any of the disclosed SACMs. The acoustic coupling medium article 1905 is attached to the housing structure 101 such that the acoustic coupling article 1905 is in contact with the external surface area of the transducer elements disposed in the housing structure 1901.

In this non-limiting example, the housing structure 1901 includes a curved section where transducer elements (not shown) of an acoustic transmit and/or receive transducer array are positioned. The curved section of the housing structure 1901 can be configured to various sizes and/or curvatures tailored to a particular body region or part where the couplant device 1900 is to be applied in acoustic imaging, measurement, and/or therapy implementations. For example, the length, depth, and arc of the curved section of the housing structure 1901 can be configured to make complete contact with a region of interest on an anatomical structure, e.g., such as a breast, arm, leg, neck, throat, knee joint, hip joint, ankle, waist, shoulder, or other anatomical structure of a human or animal (e.g., canine) subject to image or apply ultrasonic treatment to target volumes within such structures, such as splenic masses, cancerous or non-cancerous tumors, legions, sprains, tears, bone outlines and other signs of damage or maladies. For example, the curved section of the housing structure 1901 can include an aperture length in a range of a few centimeters to tens or hundreds of centimeters (e.g., such as an 18 cm baseline as depicted in FIG. 19A), an aperture depth in a range of a few centimeters to tens or hundreds of centimeters, and an arc or curvature of 1/(half or a few centimeters) to 1/(tens or hundreds of centimeters), e.g., $1/0.5\ cm^{-1}$ to $1/18\ cm^{-1}$. Notably, in some examples, the transducer section of the probe device 1900 can be flat, angled or arranged in other geometries in addition or alternative from being curved.

The acoustic coupling article 1905 is operable to conduct acoustic signals between the transducer elements of the probe device 1900 and a receiving medium (e.g., body region or part of the subject, e.g., such as the subject's midsection, head, or appendage) where the probe device 1900 is to be placed in contact to transmit and receive the acoustic signals propagating toward and from a target volume of interest in the subject. The acoustic coupling article 1905 is able to conform to the receiving medium to provide acoustic impedance matching between the transducer elements and the receiving medium (e.g., the skin of the subject, including body hair protruded from the skin).

In some embodiments of the probe device 1900, for example, the housing structure 1901 includes a flexible bracket 1902 that attaches to a portion of the housing structure 1901 body on the transducer facing side, e.g., the curved section of the housing structure 1901 body in the illustrative example in FIGS. 19A-19C. In some implementations, for example, the acoustic coupling article 1905 can be molded into the flexible bracket 1902, which can also include the acoustic coupling article 1905 being adhesively attached (e.g., glued) to the flexible bracket 1902 at portions of the acoustic coupling article 1905 away from acoustic signal propagation with the transducer elements. The flexible bracket 1902 is structured to flex such that it can conform to the receiving body that it surrounds. For example, the flexible bracket 1902 can include flexible materials, e.g., including, but not limited to, ABS plastic, polyurethane, nylon, and/or acetyl copolymer.

As illustrated in FIG. 19C, in some embodiments, the acoustic coupling article 1905 is coupled to the flexible bracket 1902 via notch attachments and/or arches. For example, the flexible bracket 1902 can include a base component 1912 to attach to the ends of the acoustic coupler 1905. In some embodiments, the base component 1912 can include clips to secure and/or adhere the acoustic coupler 1905. In the example shown in FIG. 19C, the flexible bracket 1902 includes one or more arch components 1913 configured to a size and curvature to span across the curved section of the housing structure 1901 body. The one or more arch components 1913 are positioned at one or more respective locations on the base component 1912 away from where the transducer elements are to be positioned when the flexible bracket 1902 is attached to the housing structure 1901. In some embodiments, the flexible bracket 1902 can include a pattern of notches 1914, e.g., disposed on one side of the arch component(s) 1913, to allow the flexible bracket 1902 to bend easily without breaking. The spacing of the notches 1914 can be configured based on the curvature section of the housing structure 1901. In some embodiments, for example, the flexible bracket 1902 can include an undercut lip with a chamfer, e.g., located on the other side of the arch component(s) 113, so that when it is flexed into the shape of the array and pressed into position, the chamfered lip flexes over the lip on the curved section of the housing structure 1901 and secures the flexible bracket 1902, and thereby the acoustic coupler 1905, in place.

In some implementations, for example, the acoustic coupling article 1905 can be bonded or molded into the flexible bracket 1902 when cross-linking of SACM occurs. In some implementations, for example, the SACM of the acoustic coupling article 1905 can also be molded on the subject-facing side to smooth or curve the edges, e.g., which can allow the probe device 1900 to contact and release from the subject easier.

In some embodiments, the acoustic coupling article 1905 couples to the transducers of the probe device 1900 via a flexible, overmolded bracket. For example, the bracket is imbedded in gel-sol during pour-casting; and once the gel-sol cures, the overmolded bracket 1902 can then retain the acoustic coupling article 1905 to the probe device 1900 via snap fit features on the probe device housing.

EXAMPLES

The following examples are illustrative of several embodiments of the present technology. Other exemplary embodiments of the present technology may be presented prior to the following listed examples, or after the following listed examples.

In some embodiments in accordance with the present technology (example 1), a method of manufacturing an acoustic coupling material includes (a) forming a staged solution by adding together a stock solution comprising a monomer and a polymer in deoxygenated water and a primed solution comprising a covalent crosslinking agent and a catalyst; (b) forming a gel-sol by mixing the staged solution with a first network activator solution comprising a monomer activator and a second network activator solution comprising a polymer activator; (c) dispensing the gel-sol into a mold; and (d) curing the gel-sol in the mold to produce a semi-rigid acoustic couplant, wherein the method is carried under an inert atmosphere.

Example 2 includes the method of any of examples 1-23, wherein the primed solution is added to the stock solution at about 23° C.

Example 3 includes the method of any of examples 1-23, wherein the first network activator solution and the second network activator solution are added to the staged solution at about 15° C.

Example 4 includes the method of any of examples 1-23, wherein the mold includes a plastic or a metal.

Example 5 includes the method of any of examples 1-23, wherein the plastic mold includes thermally-formed plastic, an injection-molded plastic, a casted plastic, or a machined plastic.

Example 6 includes the method of any of examples 1-23, wherein the mold includes one or more of polyethylene terephthalate glycol (PETG), acrylonitrile butadiene styrene (ABS), polyethylene terephthalate (PET), amorphous polyethylene terephthalate (APET), polycarbonate (PC), polyethylene (PE), polypropylene (PP), polystyrene (PS), crosslinked polyethylene (XLPE), or thermoplastic polyurethane (TPU).

Example 7 includes the method of any of examples 1-23, further comprising, prior to step (d), heating the gel-sol to accelerate a gelling process.

Example 8 includes the method of any of examples 1-23, further comprising, irradiating the gel-sol with light.

Example 9 includes the method of any of examples 1-23, further comprising, sterilizing the gel-sol by applying radiation.

Example 10 includes the method of any of examples 1-23, further comprising, sealing the semi-rigid acoustic couplant under an inert atmosphere to prevent oxygen adsorption.

Example 11 includes the method of any of examples 1-23, wherein the curing comprises an additional post-curing step to accelerate curing of the semi-rigid acoustic couplant, reduce an amount of residual monomer in the semi-rigid acoustic couplant, and/or to sterilize the semi-rigid acoustic couplant.

Example 12 includes the method of any of examples 1-23, further comprising, packing the semi-rigid acoustic couplant into a vehicle for shipment.

Example 13 includes the method of any of examples 1-23, wherein the stock solution is stable after preparation for at least 30 minutes.

Example 14 includes the method of any of examples 1-23, wherein the semi-rigid acoustic couplant is manufacturable on a small scale, on a large scale or on both a small and large scale.

Example 15 includes the method of any of examples 1-23, wherein the monomer includes an acrylamide.

Example 16 includes the method of example 15, wherein the acrylamide is dimethylacrylamide (DMA).

Example 17 includes the method of any of examples 1-23, wherein the copolymer includes a block copolymer comprising an alginate.

Example 18 includes the method of example 17, wherein the alginate is sodium alginate (SA).

Example 19 includes the method of any of examples 1-23, wherein the covalent crosslinking agent includes an acrylamide.

Example 20 includes the method of example 19, wherein the acrylamide is N',N'-methylene bisacrylamide (MBA).

Example 21 includes the method of any of examples 1-23, wherein the catalyst is tetramethylethylenediamine (TMED).

Example 22 includes the method of any of examples 1-23, wherein the monomer activator is ammonium persulfate (APS).

Example 23 includes the method of any of examples 1-22, wherein the polymer activator includes a block copolymer activator comprising calcium sulfate (CA).

In some embodiments in accordance with the present technology (example 24), a method of manufacturing a hydrogel includes (a) heating a first solution comprising a 1° network component and a 2° network component in deoxygenated water to lower a viscosity of the solution; (b) cooling the first solution to about 23° C. and adding a second solution comprising 1° network crosslinker and a catalyst to form a third solution; (c) optionally, adding a photoinitiator to the second solution prior to adding the second solution to the first solution; and (d) cooling the third solution to about 15° C. and adding a chilled 1° network activator solution and a chilled 2° network activator solution to the third solution simultaneously, wherein upon adding the chilled 1° network activator solution and a chilled 2° network activator solution, the 1° network component and the 2° network component polymerize to form a gel-sol; and (e) dispensing the gel-sol into a mold to form the hydrogel, wherein each of steps (a)-(e) are carried out under and inert atmosphere.

Example 25 includes the method of any of examples 24-38, wherein the solution comprising a 1° network activator and the solution comprising 2° network activator are added to the staged solution in step (c) at about 15° C.

Example 26 includes the method of any of examples 24-38, wherein the gel-sol in step (e) is dispensed into a polyethylene terephthalate glycol (PETG) tray.

Example 27 includes the method of any of examples 24-38, further comprising, placing the hydrogel into an oven and/or irradiating with light to accelerate a curing process.

Example 28 includes the method of any of examples 24-38, further comprising, sealing the hydrogel under an inert atmosphere to prevent oxygen adsorption.

Example 29 includes the method of any of examples 24-38, further comprising, packing the hydrogel packing into a vehicle for shipment.

Example 30 includes the method of any of examples 24-38, wherein the 1° network component includes an acrylamide.

Example 31 includes the method of example 30, wherein the acrylamide is dimethylacrylamide (DMA).

Example 32 includes the method of any of examples 24-38, wherein the 2° network component includes an alginate.

Example 33 includes the method of example 32, wherein the alginate is sodium alginate (SA).

Example 34 includes the method of any of examples 24-38, wherein the 1° network crosslinking agent includes an acrylamide.

Example 35 includes the method of example 34, wherein the acrylamide is N',N'-methylene bisacrylamide (MBA).

Example 36 includes the method of any of examples 24-38, wherein the catalyst is tetramethylethylenediamine (TMED).

Example 37 includes the method of any of examples 24-38, wherein the 1° network activator is ammonium persulfate (APS).

Example 38 includes the method of any of examples 24-37, wherein the 2° network activator is calcium sulfate (CA).

In some embodiments in accordance with the present technology (example 39), a method of manufacturing a hydrogel comprising sodium alginate block copolymer (P(SA)) and dimethylacrylamide monomer (DMAm) includes (a) preparing a solution comprising sodium alginate (SA) in deoxygenated water and preparing a solution comprising dimethylacrylamide (DMA) in deoxygenated water; (b) filtering the solution comprising the SA to remove aggregated SA and collecting a filtrate of the solution comprising SA; (c) adding the solution comprising DMA to the filtrate of the solution comprising SA to form a stock solution; (d) mixing the stock solution with a solution comprising N',N',N,N-tetramethylethylenediamine (TMED) and N,N'-methylene bisacrylamide (MBA) to form a staged solution; (e) adding to the staged solution a solution comprising a calcium sulfate (CA) and a solution comprising ammonium persulfate (APS) simultaneously, wherein the DMA and SA polymerize to form a gel-sol; (f) dispensing the gel-sol of the polymerized DMA and SA into a mold; (g) placing the mold into oven to cure the gel-sol and optionally, irradiating the gel-solution with light to accelerate curing to form the hydrogel; (h) sealing the hydrogel under an inert atmosphere; and (g) packing the hydrogel into a vehicle for shipment.

Example 40 includes the method of any of examples 39-45, wherein the gel-sol is irradiated with UV-radiation, γ radiation, electron beam irradiation (EBI), or combination thereof.

Example 41 includes the method of any of examples 39-45, wherein the method manufactures the hydrogel to have at least one of the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, or an engineering strain (c) of about −15 mm.

Example 42 includes the method of any of examples 39-45, wherein the method manufactures the hydrogel to have at least two of the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, or an engineering strain (c) of about −15 mm.

Example 43 includes the method of any of examples 39-45, wherein the method manufactures the hydrogel to have at least three of the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, or an engineering strain (c) of about −15 mm.

Example 44 includes the method of any of examples 39-45, wherein the method manufactures the hydrogel to have at least four of the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, or an engineering strain (c) of about −15 mm.

Example 45 includes the method of any of examples 39-44, wherein the method manufactures the hydrogel to have the following properties: a speed of sound (SOS) of about 1549 m/s, an attenuation (ATTN) of about 0.14 dB/MHz·cm, an acoustic impedance (Z) of about 1.597 MRayls, a Young's Modulus (E) of about 32 kPa, and an engineering strain (c) of about −15 mm.

In some embodiments in accordance with the present technology (example 46), an acoustic coupling article includes a semi-rigid acoustic coupling medium (SACM) operable to conform to a receiving body to propagate an acoustic signal within the SACM to and from the receiving body; and a packaging container coupled to the external layer of the SACM, the packing container including a mold casing in which the SACM is produced therein to have at least a portion of its shape defined by the mold casing.

Example 47 includes the article of any of examples 46-57, wherein the SACM is molded and cured within the packaging container and ready for shipment thereafter.

Example 48 includes the article of any of examples 46-57, wherein the mold casing encompasses all but a portion of the SACM.

Example 49 includes the article of any of examples 46-57, wherein the packaging container includes a second component to cover the portion not encompassed by the casing component.

Example 50 includes the article of any of examples 46-57, wherein the SACM is operable to propagate the acoustic signal between the receiving body and the SACM with an acoustic impedance matching of 2 MRayls or less.

Example 51 includes the article of any of examples 46-57, wherein the SACM is operable to conform to both the receiving body and an acoustic probe device having one or more transducer elements without gaps in between the external layer of the SACM and the receiving body and one or more transducers.

Example 52 includes the article of any of examples 46-57, wherein the SACM is stretchable in a range of 10% to 1000% elongation.

Example 53 includes the article of any of examples 46-57, wherein the SACM is compressible in a range of 20% to 99.9%.

Example 54 includes the article of any of examples 46-57, wherein the SACM includes an elasticity with a Young's modulus in a range of 30 kPa to 500 kPa.

Example 55 includes the article of any of examples 46-57, wherein the SACM includes biocompatible materials.

Example 56 includes the article of any of examples 46-57, wherein the SACM is sterile within the packaging container.

Example 57 includes the article of any of examples 46-56, wherein the SACM is clean and non-sterile within the packaging container.

Example 58 includes the article of any of examples 46-57, wherein the article is manufactured by the method of any of examples 1-23.

Example 59 includes the article of any of examples 46-57, wherein the article is manufactured by the method of any of examples 24-38.

Example 60 includes the article of any of examples 46-57, wherein the article is manufactured by the method of any of examples 39-45.

All numerical designations, e.g., pH, temperature, time, concentration, and molecular weight, including ranges, are approximations which are varied (+) or (−) by increments of 1.0 or 0.1, as appropriate, or alternatively by a variation of +1-15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method of manufacturing and distributing an acoustic coupling material packaged for ultrasound imaging, the method comprising:
    (a) forming a staged solution by adding together a stock solution comprising a monomer and a polymer in deoxygenated water and a primed solution comprising a covalent crosslinking agent and a catalyst;
    (b) forming a gel-sol by mixing the staged solution with a first network activator solution comprising a monomer activator and a second network activator solution comprising a polymer activator;
    (c) dispensing the gel-sol into a mold;
    (d) curing the gel-sol in the mold to produce a semi-rigid acoustic couplant,
    wherein (a)-(d) of the method is carried under an inert atmosphere; and
    (e) sterilizing the gel-sol in the mold by applying radiation including gamma radiation (g-ray) to produce a sterilized semi-rigid acoustic couplant;
    wherein the mold packages the sterilized semi-rigid acoustic couplant and provides a sterile barrier against microbes and maintains moisture of the sterilized semi-rigid acoustic couplant.

2. The method of claim 1, wherein the primed solution is added to the stock solution at about 23° C.

3. The method of claim 1, wherein the first network activator solution and the second network activator solution are added to the staged solution at about 15° C.

4. The method of claim 1, wherein the mold includes a plastic or a metal.

5. The method of claim 4, wherein the plastic mold includes thermally-formed plastic, an injection-molded plastic, a casted plastic, or a machined plastic.

6. The method of claim 1, wherein the mold includes one or more of polyethylene terephthalate glycol (PETG), acrylonitrile butadiene styrene (ABS), polyethylene terephthalate (PET), amorphous polyethylene terephthalate (APET), polycarbonate (PC), polyethylene (PE), polypropylene (PP), polystyrene (PS), cross-linked polyethylene (XLPE), or thermoplastic polyurethane (TPU).

7. The method of claim 1, further comprising:
    prior to step (d), heating the gel-sol to accelerate a gelling process.

8. The method of claim 7, further comprising:
    irradiating the gel-sol with light.

9. The method of claim 1, further comprising:
    sealing the semi-rigid acoustic couplant under an inert atmosphere to prevent oxygen adsorption.

10. The method of claim 1, wherein the curing comprises an additional post-curing step to accelerate curing of the semi-rigid acoustic couplant, reduce an amount of residual monomer in the semi-rigid acoustic couplant, and/or to sterilize the semi-rigid acoustic couplant.

11. The method of claim 1, further comprising:
packing the semi-rigid acoustic couplant into a vehicle for shipment.

12. The method of claim 1, wherein the stock solution is stable after preparation for at least 30 minutes.

13. The method of claim 1, wherein the monomer includes an acrylamide.

14. The method of claim 13, wherein the acrylamide is dimethylacrylamide (DMA).

15. The method of claim 1, wherein the polymer includes a block copolymer comprising an alginate.

16. The method of claim 15, wherein the alginate is sodium alginate (SA).

17. The method of claim 1, wherein the covalent cross-linking agent includes an acrylamide.

18. The method of claim 17, wherein the acrylamide is N',N'-methylene bisacrylamide (MBA).

19. The method of claim 1, wherein the catalyst is tetramethylethylenediamine (TMED).

20. The method of claim 1, wherein the monomer activator is ammonium persulfate (APS).

21. The method of claim 1, wherein the polymer activator includes a block copolymer activator comprising calcium sulfate (CA).

22. The method of claim 1, wherein the mold in which the gel-sol is dispensed includes polyethylene terephthalate glycol (PETG) and is transparent to g-ray.

23. The method of claim 1, wherein the mold includes a mold casing in which the semi-rigid acoustic couplant is produced therein to have at least a portion of its shape defined by the mold casing and a cover component to cover a portion of the semi-rigid acoustic couplant not encompassed by the casing component.

* * * * *